US006124097A

United States Patent [19]
van Eekelen et al.

[11] Patent Number: 6,124,097
[45] Date of Patent: *Sep. 26, 2000

[54] STABLE GENE AMPLIFICATION IN CHROMOSOMAL DNA OF PROKARYOTIC MICROORGANISMS

[75] Inventors: Christiaan A. G. van Eekelen, Nuenen; Johannes C. Van Der Laan, Schiedam; Leo J. S. M. Mulleners, Rijen, all of Netherlands

[73] Assignee: DSM N.V., Heerlen, Switzerland

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 09/049,867

[22] Filed: Mar. 27, 1998

Related U.S. Application Data

[63] Continuation of application No. 08/295,082, Aug. 24, 1994, Pat. No. 5,733,723, which is a continuation of application No. 07/893,601, Jun. 3, 1992, abandoned, which is a continuation of application No. 07/653,977, Feb. 11, 1991, abandoned, which is a continuation of application No. 07/162,105, Feb. 29, 1988, abandoned.

[30] Foreign Application Priority Data

Feb. 27, 1987 [EP] European Pat. Off. .............. 87200356

[51] Int. Cl.[7] .............................. C12Q 1/68; C12N 1/21; C12P 21/02

[52] U.S. Cl. ....................... 435/6; 435/69.1; 435/320.1; 435/252.3; 435/252.31; 435/252.33; 435/252.34; 435/252.35; 435/212; 435/219; 435/222

[58] Field of Search ..................... 435/69.1, 5, 320.1, 435/252.3, 252.31, 252.2, 6, 212, 219, 222, 252.33, 252.34, 252.35

[56] References Cited

U.S. PATENT DOCUMENTS

| Re. 30,602 | 5/1981 | TeNijenhuis | 510/306 |
|---|---|---|---|
| 4,469,791 | 9/1984 | Colson et al. | 435/252.31 |
| 4,959,316 | 9/1990 | Stanislas et al. | 435/6 |
| 5,733,723 | 3/1998 | van Eekelen | 435/6 |

FOREIGN PATENT DOCUMENTS

| 0 032 238 | 7/1981 | European Pat. Off. . |
|---|---|---|
| 0 074 553 | 3/1983 | European Pat. Off. . |
| 0 124 374 | 7/1984 | European Pat. Off. . |
| 0 127 328 | 12/1984 | European Pat. Off. . |
| 0 134 048 | 3/1985 | European Pat. Off. . |
| 0 130 756 | 9/1985 | European Pat. Off. . |
| 0 205 371 | 12/1986 | European Pat. Off. . |
| 1 519 148 | 11/1974 | United Kingdom . |
| WO 86/01825 | 3/1986 | WIPO . |
| WO 87/04461 | 7/1987 | WIPO . |

OTHER PUBLICATIONS

James E. Bailey, Science, vol. 252, pp. 1668–1675, Jun. 21, 1991.

Anagnostopoulos et al., "The Genetic Map of *Bacillus subtilis*", In Sonenshein et al. (eds.), *B. Subtilis and Other Gram–Positive Bacteria: Biochemistry, Physiology, and Molecular Genetics* (Amer. Soc. for Microbiol., Washington, D.C. pp. 425–461 (1993)).

Baigori et al., *J. Bacteriol.*, 173, 4240–4242 (1991).

Ferrari et al., *Mol. Gen. Genet.*, 189, 321–325 (1983).

Haldenwang et al., *J. Bacteriol.* 142, 90–98 (1980).

Henner et al., *Microbiol. Rev.*, 44, 57–82 (1980).

Hilden et al., *J. Bacteriol.*, 177, 7280–7284 (1995).

Kallio et al., *Appl. Microbiol. Biotechnol.*, 27, 64–71 (1987).

Ogasawara et al., *Nucl. Acid Res.*, 14, 9989–9999 (1986).

Ott et al., *J. Bacteriol.*, 165, 951–957 (1986).

Schneider et al., *Genetics*, 101, 189–210 (1982).

Schneider et al., *J. Gen Microbiol.*, 129, 687–701 (1983).

Schneider et al., *J. Gen. Microbiol.*, 125, 241–256 (1981).

Winnacker, Gene und Klone, *Verlag Chemie Weinheim*, 158–161 (1984) (with attached explanation of relevance, and missing p. 159).

Khasanov et al., *Biological Abst.*, 81, 81548 (1986).

Yu et al., *Biological Abst.*, 82, 86427 (1986).

Hofemeister et al., *Chem. Abst.*, 98, 155686a (1983).

Kallio et al., *Chem. Abst.*, 108, 88925n (1988).

Croft, L.R., "A Compilation of Amino Acid Sequences of Proteins with an Introduction to the Methodology," *Handbook of Protein Sequence Analysis*, 198–199 (1980).

(List continued on next page.)

*Primary Examiner*—David Guzo
*Attorney, Agent, or Firm*—McDonnell Boehnen Hulbert & Berghoff

[57] ABSTRACT

Transformed prokaryotic hosts are provided comprising two or more copies of a DNA sequence stably maintained in their chromosome, said DNA sequence comprising a gene encoding a polypeptide of interest wherein said copies are separated by endogenous chromosomal DNA sequences. Methods are also provided for producing said transformed host strains. The transformed host strains are capable of increased production of the polypeptide of interest compared to host strains which already produce said polypeptide. Preferred host strains are Bacillus novo species PB92 which produces a high-alkaline proteolytic enzyme and *B. licheniformis* strain T5 which produces a thermostable α-amylase, and mutants and variants of said strains. Preferred poly-peptide encoding genes are the protease encoding gene obtainable from Bacillus PB92 and the α-amylase encoding gene obtainable from *B. licheniformis* strain T5.

24 Claims, 23 Drawing Sheets

OTHER PUBLICATIONS

Honorouchi et al., "Nucleotide Sequence and Functional Map of pE194, a Plasmid that Specifies Inducible Resistance to Macrolide, Lincosamide, and Streptogramin Type B Antibiotics", *J. Bacteriol.*, 150, 804–814 (1982).

Makino et al., *Agric. Biol. Chem.*, 50, 501–504 (1986).

Mannarelli et al., *J. Bacteriol.*, 160, 867–873 (1984).

Niaudet et al., *J. Bacteriol.*, 163, 111–120 (1985).

Prozorov et al., *Gene*, 34, 39–46 (1985).

Saunders et al., Use of Chromosomal Integration in the Establishment and Expression of blaZ, a *Staphylococcus aureus* β–Lactamase Gene, in *Bacillus subtilis, J. Bacteriol.*, 157, 718–726 (1984).

Van der Laan et al., "Stable Chromosomal Gene Amplification", In: *Genetic Transformation and Expression*, ed. Butler et al. (1990).

Williams et al., *Gene*, 24, 37–51 (1983).

```
                                           260                        280                          300
GAAGCTGTCAGTGAGTTTGTAGAACAAGTAGAGGCAAATGACGAGAGGTCGCCATTCTCT
GluAlaValSerGluPheValGluGlnValGluAlaAsnAspGluValAlaIleLeuSer 320                                3
                                                                      340                          360
GAGGAAGAGGAAGTCGAAATTGAATTGCTTCATGAATTGAAACGATTCCTGTTTTATCC
GluGluGluGluValGluIleGluLeuLeuHisGluLeuLysArgPheLeuPheLeuSer 380                        400                          420
GTTGAGTTAAGCCCAGAGAAGATGTGGACGCGCTTGAACTCGATCCAGCGATTTCTTATATT
ValGluLeuSerProGluLysMetTrpThrArgLeuAsnSerIleGlnArgPheLeuTyrIle
                                                     mat     4
                                                            460
                                           440                                                    480
GAAGAGGATGCAGAAGTAACGACAATGGCGCAATCAGTGCCATGGGAATTAGCCGTGTG
GluGluAspAlaGluValThrThrMetAlaGlnSerValProTrpGlyIleSerArgVal
```

FIG. 5B

```
                                                    540
                    520
500
CAAGCCCCAGCTGCCCATAACCGTGGATTGACAGGTTCTGGTGTAAAAGTTGCTGTCCTC
GlnAlaProAlaAlaHisAsnArgGlyLeuThrGlySerGlyValLysValAlaValLeu
                                                    600
                    580
  560
                    5
GATACAGGTATTTCCACTCATCCAGACTTAAATATTCGTGGTGGCGCTAGCTTTGTACCA
AspThrGlyIleSerThrHisProAspLeuAsnIleArgGlyGlyAlaSerPheValPro
                                                    660
                    640
620
GGGGAACCATCCACTCAAGATGGGAATGGGCATGGCACGCATGTGGCTGGACGATTGCT
GlyGluProSerThrGlnAspGlyAsnGlyHisGlyThrHisValAlaGlyThrIleAla
  6                 680
                                                    720
                    700
GCTTTAAACAATTCGATTGGCGTTCTTGGCGTAGCACCGAACGCGGAACTATACGCTGTT
AlaLeuAsnAsnSerIleGlyValLeuGlyValAlaProAsnAlaGluLeuTyrAlaVal
```

FIG. 5C

```
                    740                    760                    780
AAAGTATTAGGGGCGAGCGGTTCAGGTTCGGTCAGCTCGATTGCCCAAGGATTGGAATGG
LysValLeuGlyAlaSerGlySerValSerSerIleAlaGlnGlyLeuGluTrp
                ────────7────────
                    800                    820                    840
GCAGGGAACAATGGCATGCACGTTGCTAATTTGAGTTTAGGAAGCCCTTCGCCAAGTGCC
AlaGlyAsnAsnGlyMetHisValAlaAsnLeuSerLeuGlySerProSerAla
                    860                    880                    900
ACACTTGAGCAAGCTGTTAATAGCGCGACTTCTAGAGGCGTTCTTGTTGTAGCGGCATCT
ThrLeuGluGlnAlaValAsnSerAlaThrSerArgGlyValLeuValValAlaAlaSer
                    920                    940                    960
                ────────8────────
GGGAATTCAGGTGCAGGCTCAATCAGCTATCCGGCCCGTTATGGAACGCAATGGCAGTC
GlyAsnSerGlyAlaGlySerIleSerTyrProAlaArgTyrAlaAsnAlaMetAlaVal
```

FIG. 5D

```
                                 980                    1000                   1020
GGAGCTACTGACCAAAACAACAACCGGCGCCAGCTTTTCACAGTATGGCGCAGGGCTTGAC
GlyAlaThrAspGlnAsnAsnAsnArgAlaSerPheSerGlnTyrGlyAlaGlyLeuAsp 9              1040                   1060                   1080
ATTGTCGCACCAGGTGTAAACGTGCAGAGACACATACCCAGGTTCAACGTATGCCAGCTTA
IleValAlaProGlyValAsnValGlnSerThrTyrProGlySerThrTyrAlaSerLeu 1100                   1120         10    1140
AACGGTACATCGATGGCTACTCCTCATGTTGCAGGTGCAGCAGCCCTTGTTAAACAAAAG
AsnGlyThrSerMetAlaThrProHisValAlaGlyAlaAlaAlaLeuValLysGlnLys 1160                   1180                   1200
AACCCATCTTGGTCCAATGTACAAATCCGCAATCATCTAAAGAATACGGCAACGAGCTTG
AsnProSerTrpSerAsnValGlnIleArgAsnHisLeuLysAsnThrAlaThrSerLeu
```

FIG. 5E

```
                                                  1260
GGAAGCACGAACTTGTATGGAAGCGGACTTGTCAATGCAGAAGCGGCAACACGCTAATCA
GlySerThrAsnLeuTyrGlySerGlyLeuValAsnAlaGluAlaAlaThrArg

1320
ATAAAAACGCTGTGCTTAAAGGGCACAGCGTTTTTTTGTGTATGAATCGAAAAGAGAAC
term
```

FIG. 5F

STABLE GENE AMPLIFICATION IN CHROMOSOMAL DNA OF PROKARYOTIC MICROORGANISMS

CROSS REFERENCE TO RELATED APPLICATIONS

This application is a continuation of U.S. Ser. No. 08/295,082, filed Aug. 24, 1994, issued Mar. 31, 1998 as U.S. Pat. No. 5,733,723, which is a continuation of U.S. Ser. No. 07/893,601, filed Jun. 3, 1992, now abandoned, which is a continuation of U.S. Ser. No. 07/653,977, filed Feb. 11, 1991, now abandoned, which is a continuation of U.S. Ser. No. 07/162,105, filed Feb. 29, 1988.

INTRODUCTION

1. Technical Field

The field relates to prokaryotic cells in which stable gene amplification is obtained by scattered non-tandem integration of at least two copies of a defined DNA sequence into the chromosome of said prokaryotic cell.

2. Background

Bacilli have been widely used for the production of industrially important enzymes such as α-amylase, neutral protease and alkaline or serine proteases (cf. Debabov, "The Industrial Use of Bacilli", in: The Molecular Biology of Bacilli, Acad. Press, New York, 1982). Improvement of production of Bacillus enzymes can be achieved both by classical genetic techniques, such as mutation and subsequent selection, and by modern molecular biological techniques. In the latter case, several ways of obtaining high levels of expression of homologous and heterologous genes in certain prokaryotic and eukaryotic microorganisms by genetic engineering have been well documented.

One of the approaches to achieve high level expression of a gene is to provide the gene with efficient regulatory sequences. Another approach, often used in combination with the first approach, is to increase the copy number of the gene in question. Amplification is primarily achieved by inserting the gene into a multicopy extrachromosomal DNA molecule such as a plasmid. However, a significant drawback of using plasmids as vectors for expressing and amplifying genetic information has been their instability. For large scale use, stability of the amplified gene is a prerequisite for maintaining high level production of the expression product encoded by the amplified gene, as many cell divisions have to take place before sufficient biomass is formed for obtaining substantial product formation.

Instability is encountered in two forms: segregational instability, where loss of the plasmid occurs during cultivation; and structural instability, where a part of the plasmid is deleted. Segregational instability can occur, for example, when a host cell is harboring a vector carrying a gene that is overexpressed. Generally there will be selective pressure towards cells that have lost the capacity to overexpress the gene, since overexpression is an unfavorable property for the transformed host cell. A large amount of metabolic energy is spent on the overexpressed gene product, which negatively influences the cells' competitiveness (growth rate) with host cells not likewise overexpressing.

A method used to counter segregational instability is to select for cells containing multicopy plasmids which carry genes which confer an advantage on the plasmid containing cell, for example, conferring resistance to an antibiotic and then to add the relevant antibiotic to the fermentation broth. However, antibiotics are generally not a useful selection means in large scale commercial production processes due to regulations concerning the approval of the fermentation process or the product itself.

Another method used to minimize plasmid loss due to segregational instability is to insert a gene which is functionally essential for the host cell into the vector (Ferrari et al., *Biotechnology* (1985) 3: 1003–1007). However, this method does not ensure structural stability of the vector.

Techniques used to solve the problem of structural plasmid instability have included avoiding expression of the gene during the phase of exponential growth, for example, by using regulatory sequences such as temperature-sensitive regulatory sequences for gene expression. Other methods used have included avoiding the use of autonomously replicating vector molecules and instead using techniques which favor integration of the introduced DNA into the host cell chromosome.

Methods of achieving integration of foreign DNA into the host cell chromosome have included homologous recombination and illegitimate recombination. Two ways of inserting DNA sequences into specific locations on a chromosome by homologous recombination are Campbell type homologous recombination and double reciprocal recombination, which are shown in FIGS. 1A and 1B, respectively. A third way of introducing DNA sequences into the chromosome, this method using a two-step replacement mechanism, is shown in FIG. 1C. In principle, a Campbell-type recombination is used, but the final result is a chromosomal arrangement that contains no duplicated sequences, and thus no amplifiable unit, in the recombined part of the chromosome. It therefore resembles a double reciprocal recombination.

Apart from using homologous recombination for the integration of foreign DNA into the chromosome it is also possible to integrate DNA by illegitimate recombination. Integrated vector molecules can be selected for under conditions which inhibit autonomous replication of non-integrated vector molecules. Use of illegitimate recombination for integration is depicted in FIG. 1D. The absence of tandem duplications in the obtained chromosomal sequence arrangements make the pathways shown in FIGS. 1B, C and D preferred for stable introduction of DNA sequences into the genome. Chromosomally integrated genes have included both homologous and heterologous genes where the amplification of the chromosomally integrated DNA has been in a tandem array. These chromosomally amplified sequences have been reported to be unstable although stability has been reported in some cases. It is therefore desirable to develop methods whereby DNA integrated into the chromosome is stably maintained.

Relevant Literature

Integration of exogenous DNA by homologous recombination into the chromosome of *Bacillus subtilis* has been described by Duncan et al., *Proc. Natl. Acad. Sci. USA* (1978) 75:3664–3668 and for *Anacystis nidulans* by Williams and Szalay, Gene (1983) 24:37–51 and in International Patent Application WO 84/00381. Integration by homologous recombination of a heterologous gene, which cannot be maintained stably when carried on a plasmid vector, into the chromosome of a microorganism is described in EP-A-0127328.

Amplification of chromosomally integrated genes, both homologous and heterologous has been documented. See, for example: Saito et al., *Proceedings of the Fourth International Symposium on Genetics of Industrial Microorganisms,* Kyoto, Japan, 1982, pp. 125130; Young, *J. Gen. Microbiol.* (1984) 130:1613–1621; Janniere et al., *Gene* (1985) 40:47–55; Sargent and Bennett, *J. Bacteriol.*

(1985) 161:589–595; Gutterson and Koshland, *Proc. Natl. Acad. Sci. USA* (1983) 80: 4894–4898; Hashiguchi et al., *Agric. Biol. Chem.* (1985) 49:545–550; Wilson and Morgan, *J. Bacteriol.* (1985) 163:445–453; French Patent Application No. 84.06701; and EP-A-0134048. Spontaneous amplification in prokaryotic cells has been reported and can be selected for. See for example the review by Anderson and Roth, *Ann. Rev. Microbiol.* (1977) 31:473–505.

In all cases referred to above, amplification of chromosomally integrated DNA was in a tandem array. This type of chromosomal amplification sequence has been reported to be unstable, although rather good stability was found in some cases, as discussed by Janniere et al., *Gene* (1985) 40:47–55.

Stabilization of naturally occurring amplified prokaryotic genes due to the presence of other essential genes between these amplified sequences has been reported. For example, of the 9 to 10 copies of the ribosomal RNA gene sets occurring in the *B. subtilis* chromosome, two tandemly located sets were separated by a cluster of tRNA genes (Wawrousek and Hansen, *J. Biol. Chem.* (1983) 258: 291–298). In other cases, naturally occurring tandemly repeated ribosomal RNA operons were deleted, both in *E. coli* and in *B. subtilis*, with little effect on the phenotypic properties of the organism: Ellwood and Momura, *J. Bacteriol.* (1980) 143:1077–1080 and Loughney et al., *J. Bacteriol.* (1983) 154:529–532, respectively.

Integration of plasmids into the chromosome of *B. subtilis* by illegitimate recombination using the vector pE194 has been described by Hofemeister et al., *Mol. Gen. Genet.* (1983) 189:58–68 and Prorozov et al., *Gene* (1985) 34:39–46.

Several genes for extracellular enzymes of bacilli have been successfully cloned, such as the α-amylase genes of *B. amyloliquefaciens* (Palva et al., *Gene* (1981) 15:43–51), *B. licheniformis* (Ortlepp, *Gene* (1983) 23:267), *B. stearothermophilus* (Mielenz et al., *Proc. Natl. Acad. Sci. USA* (1983) 80:5975–5979; EPA-0057976) and *B. subtilis* (Yang et al., *Nucleic Acids Res.* (1983) 11:237); the levansucrase gene of *B. subtilis* (Gay et al., *J. Bacteriol.* (1983) 153:1424); the neutral protease encoding genes of *B. stearothermophilus* (Fuji et al., *J. Bacteriol.* (1983) 156:831), *B. amyloliquefaciens* (Honjo et al., *J. Biotech.* (1984) 1:165) and of *B. subtilis* (Yang et al., *J. Bacteriol.* (1984) 160:115); the serine or alkaline protease encoding genes of *B. subtilis* (Wong et al., *Proc. Natl. Acad. Sci. USA* (1984) 81:1184), *B. licheniformis* (Jacobs et al., *Nucleic Acids Res.* (1985) 13:8913) and *B. amyloliquefaciens* (Wells et al., *Nucleic Acids Res.* (1983) 11:7911).

Protoplast transformation for several species of gram positive microorganisms has been reported. For *B. subtilis* a protocol for protoplast transformation was described by Chang and Cohen (*Mol. Gen. Genet.* (1979) 168:111–115), which has been widely used. Similar successful protocols have been described for the transformation of *B. megaterium* protoplasts (Vorobjeva et al., *FEMS Microbiol. Letters* (1980) 7:261–263), *B. amyloliquefaciens* protoplasts (Smith et al., *Appl. and Env. Microbiol.* (1986) 51:634), *B. thuringiensis* protoplasts (Fisher et al., *Arch. Microbiol.* (1981) 139:213–217), *B. sphaericus* protoplasts (McDonald, *J. Gen. Microbiol.* (1984) 130:203), and *B. larvae* protoplasts (Bakhiet et al., *Appl. and Env. Microbiol.* (1985) 49:577); in the same publication unsuccessful results were reported for *B. popillae*. The protocol was successful for *B. polymyxa*, *B. licheniformis*, *B. macerans* and *B. laterosporus*, but not for *B. coagulans*, *B. cereus* and *B. pumilus* even though good protoplast formation was observed (Mann et al., *Current Microbiol.* (1986) 13:131–135).

Other methods of introducing DNA into protoplasts include fusion with DNA containing liposomes (Holubova, *Folia Microbiol.* (1985) 30:97), or protoplast fusion using a readily transformable organism as an intermediate host cell (EPA-0134048).

SUMMARY OF THE INVENTION

Prokaryotic host cells, and methods for their preparation, are provided which comprise at least two copies of a DNA sequence encoding a polypeptide of interest stably integrated into the host cell chromosome. Stable maintenance of the exogenous DNA sequence is obtained by integrating two or more copies of the sequence into the host cell chromosome wherein the copies are separated by endogenous chromosomal DNA sequences.

T is the target sequence, i.e., DNA sequences present on chromosome and plasmid, between which homologous recombination can take place.

S stands for the DNA sequence to be integrated in the chromosome.

M stands for a marker gene sequence used for the selection of recombinant strain.

Figure 2A:
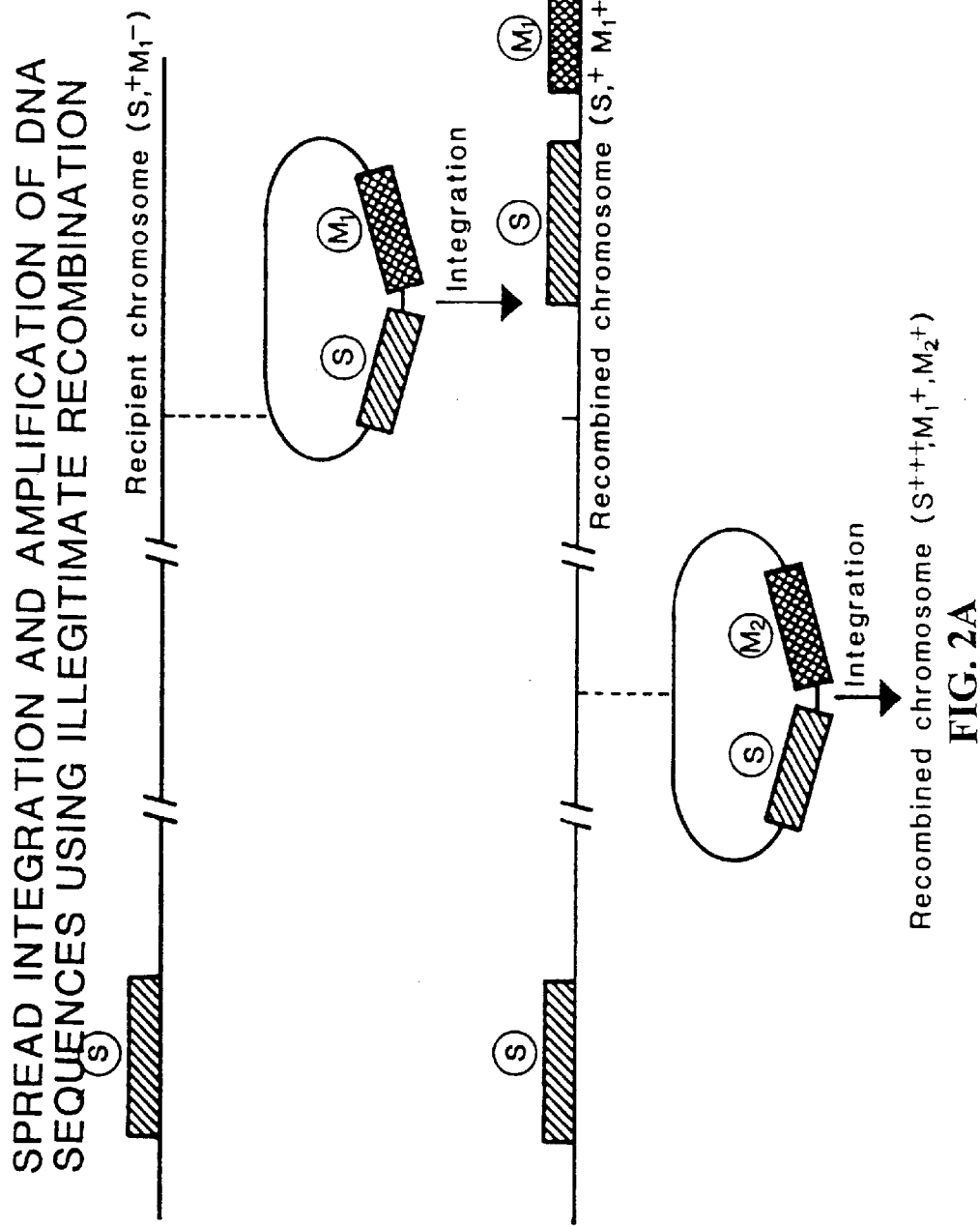
Figure 2B:
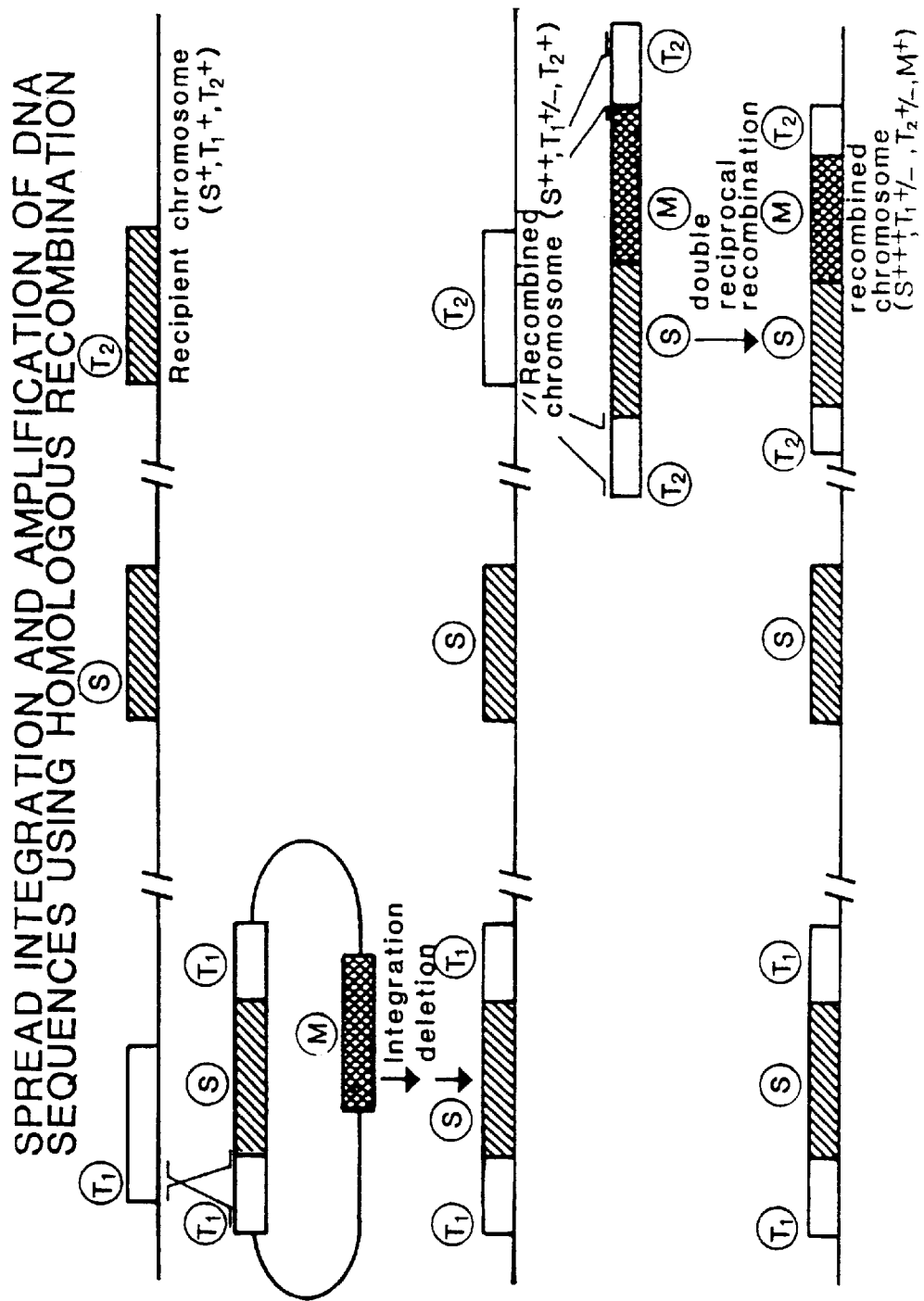

FIGS. 2A and 2B are schematic representations of two ways for obtaining stable gene amplification in a prokaryotic chromosome.

Figure 3:
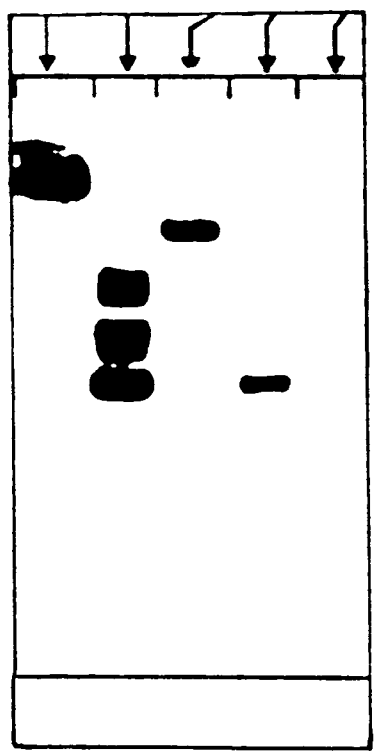

FIG. 3 shows the results of histidine/MOPS gel electrophoresis performed on supernatant from cultures of *B. subtilis* DB104 containing pUB110 and pM58, respectively, compared with several subtilisins:

Lane 1: Carlsberg subtilisin.
Lane 2: Bacillus PB92 protease.
Lane 3: *B. subtilis* subtilisin.
Lane 4: *B. subtilis* DB104 (pM58).
Lane 5: *B. subtilis* DB104 (pUB110).

Figure 4:
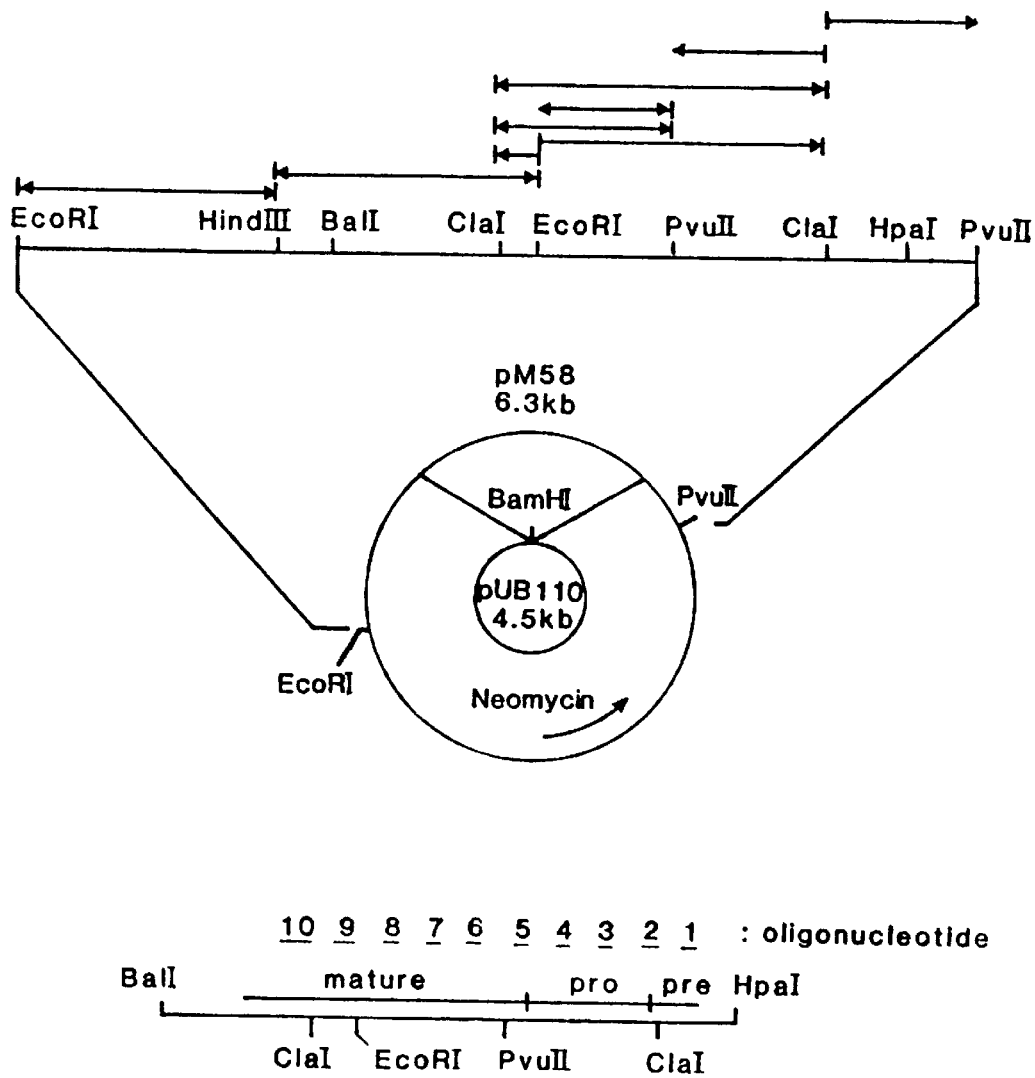
Figure 5A:
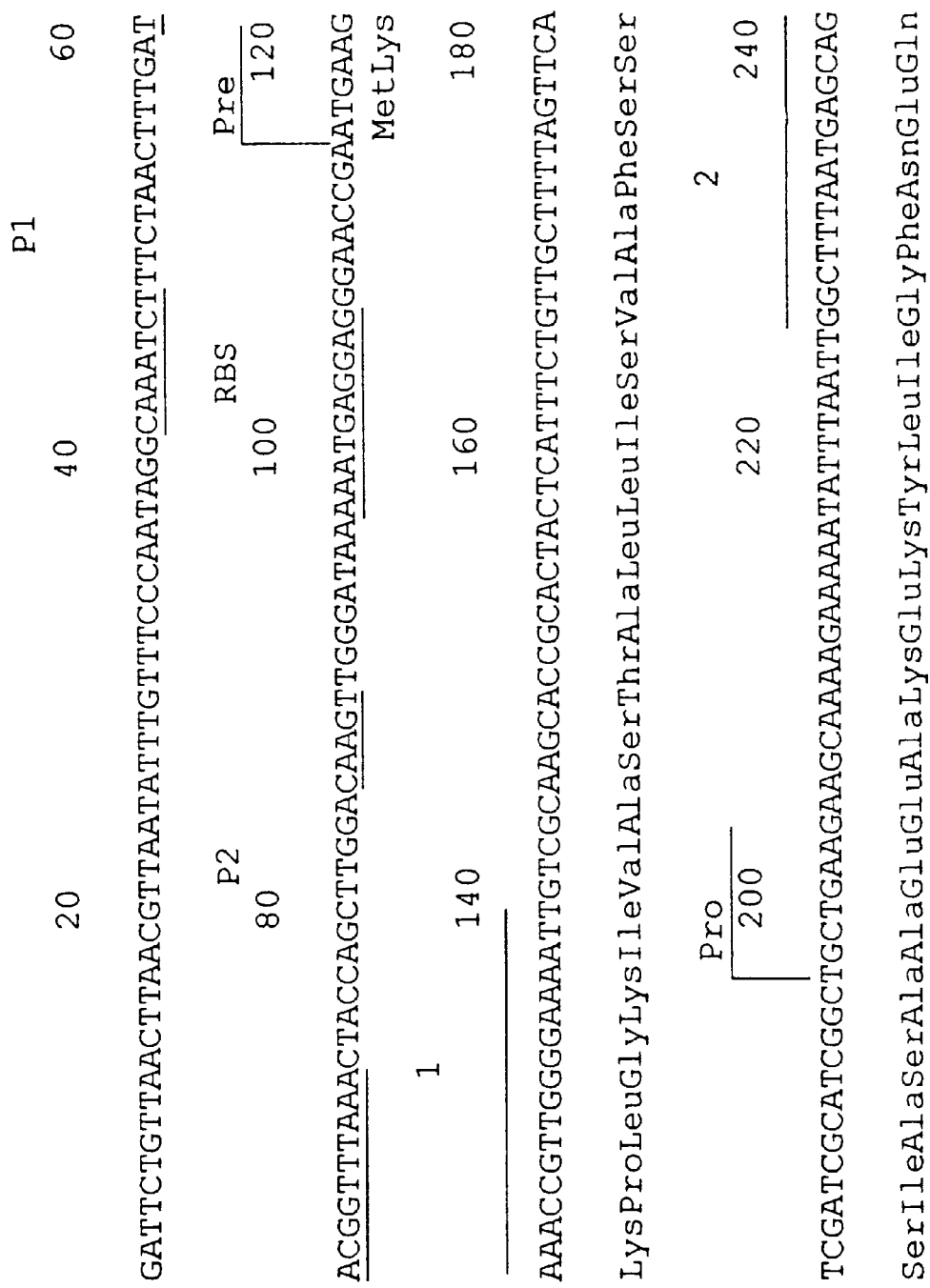

FIG. 4 shows the restriction map of plasmid pM58. Furthermore, the sequencing strategy is shown in the upper part of the figure. The arrowed solid lines represent the fragments cloned in the phage M13 vectors mp10, mp11 and mp18. The lower part of the figure shows the sequencing strategy using ten oligonucleotides located at regular distances on the protease gene.

FIGS. 5A–F shows the nucleotide sequence (SEQ ID NO:1) of the coding strand correlated with the amino acid sequence (SEQ ID NO:2) of Bacillus PB92 serine protease. Promoters ($P_1$, $P_2$), ribosome binding site (rbs) and termination regions (term) of the DNA sequence are also shown. The numbered solid lines represent the location of the ten oligonucleotides used for sequencing.

Figure 6A:
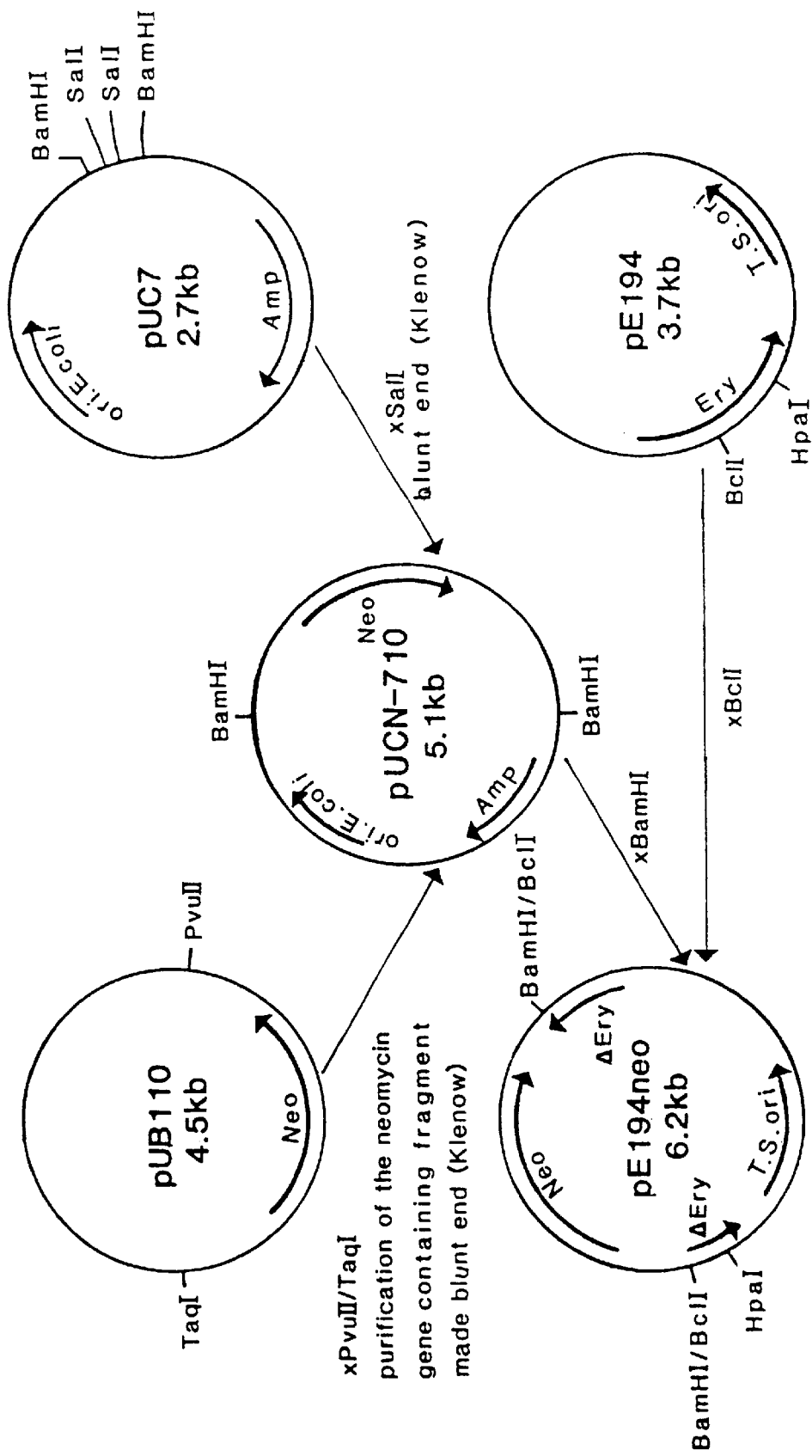
Figure 6B:
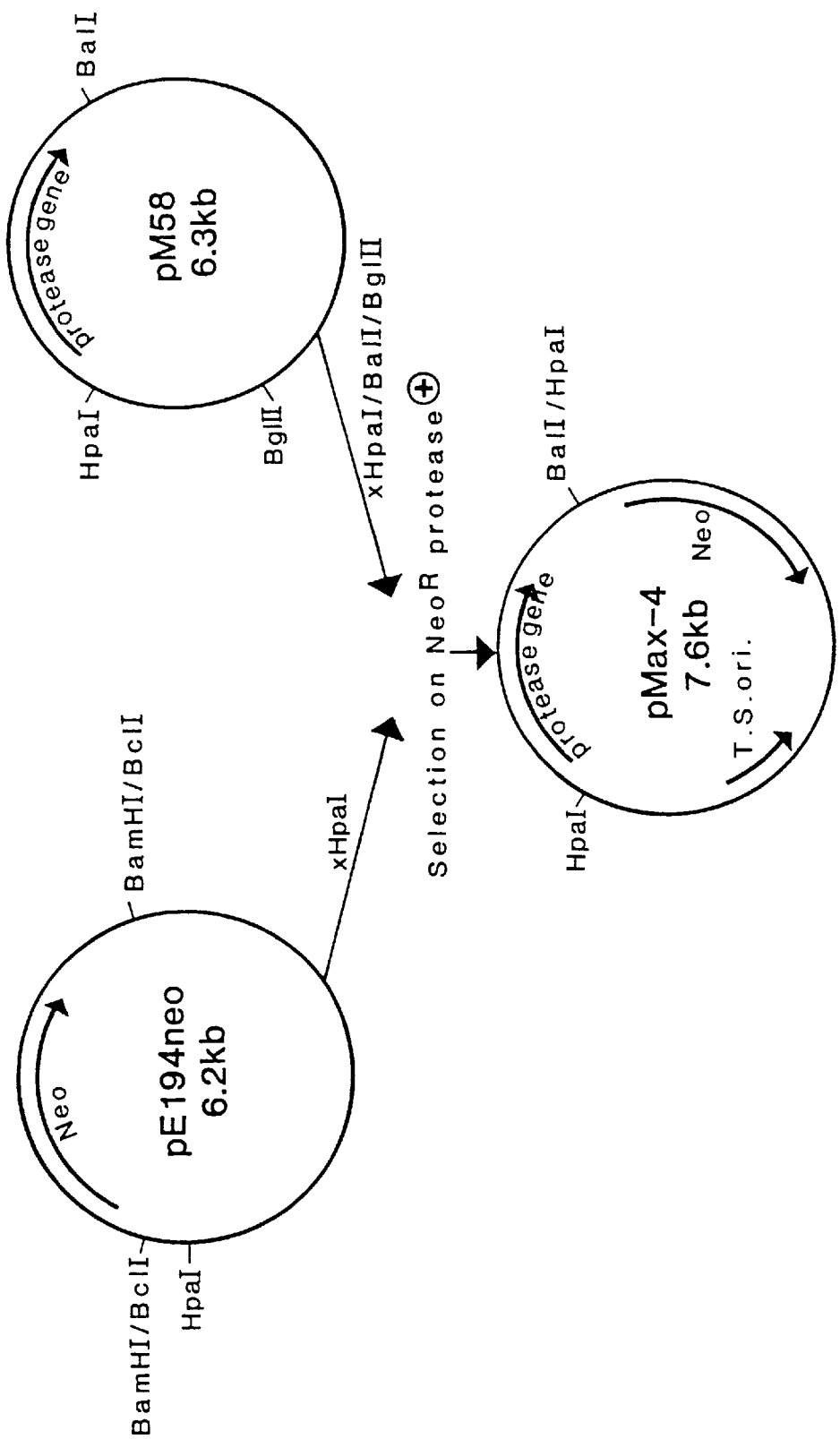
Figure 7A:
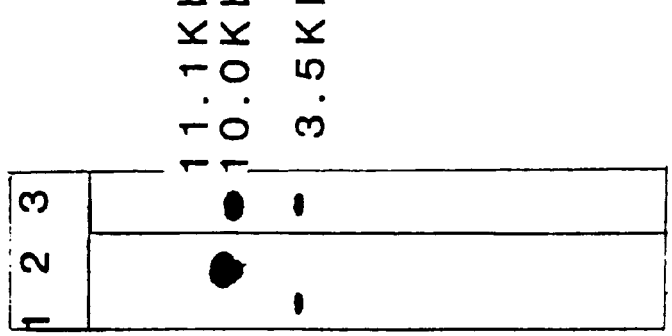

FIG. 6A shows the construction of plasmid pE194-neo.
FIG. 6B shows the construction of plasmid pMAX-4.
FIG. 7A: Digests prepared with HindIII of chromosomal DNA of the strains PB92, PBT109 and PBT108 were subjected to electrophoresis on a 0.5% agarose gel, transferred to nitrocellulose as described by Southern and hybridized with $^{32}P$ labeled nick-translated pM58 DNA. The figure shows an autoradiograph.

Figure 7B:
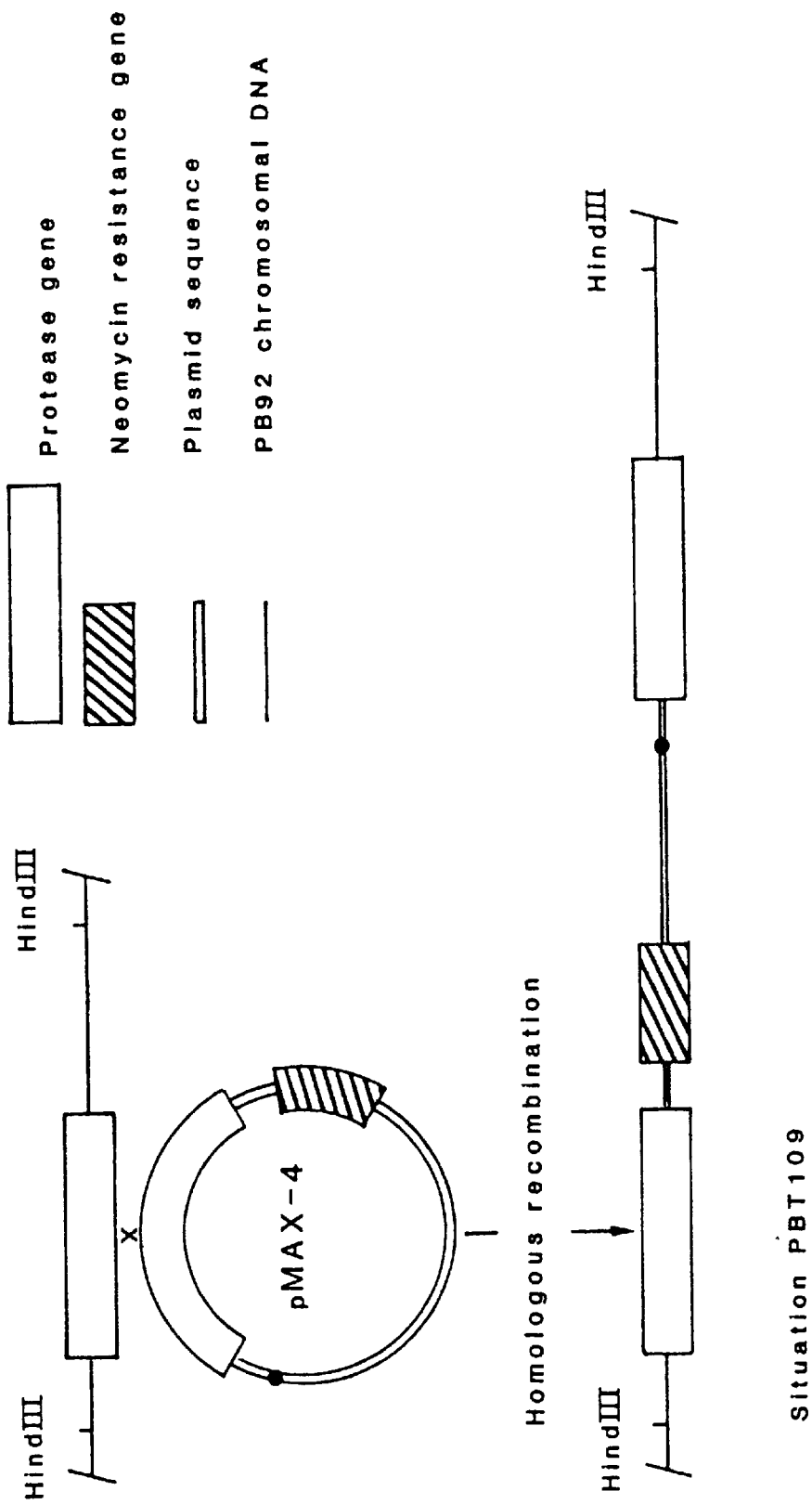
Figure 7C:
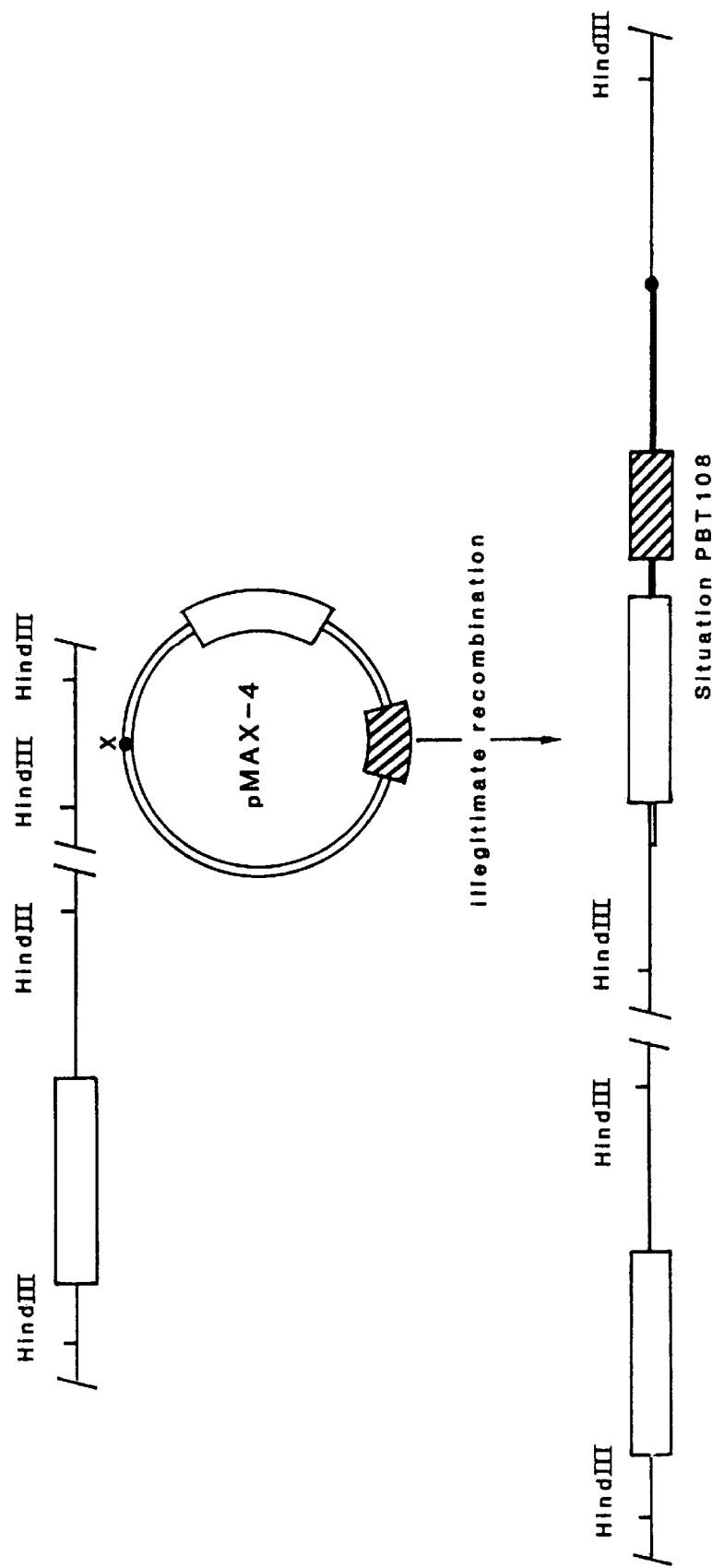

FIGS. 7B and 7C illustrate the integration events occurring in case of homologous (B) recombination and illegitimate (C) recombination between pMAX-4 and the Bacillus PB92 chromosome.

Figure 8:
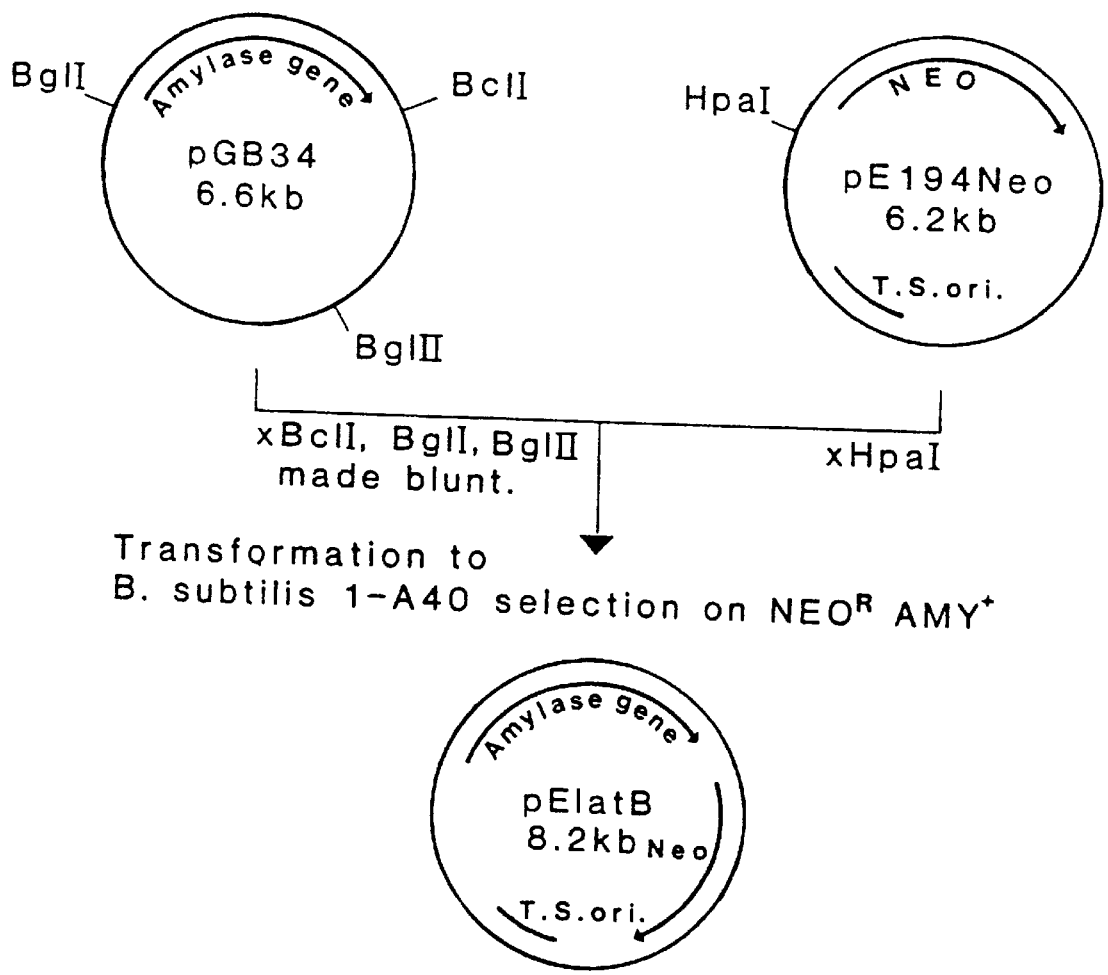

FIG. 8 shows the construction of integration vector pE1atB.

Figure 9A:
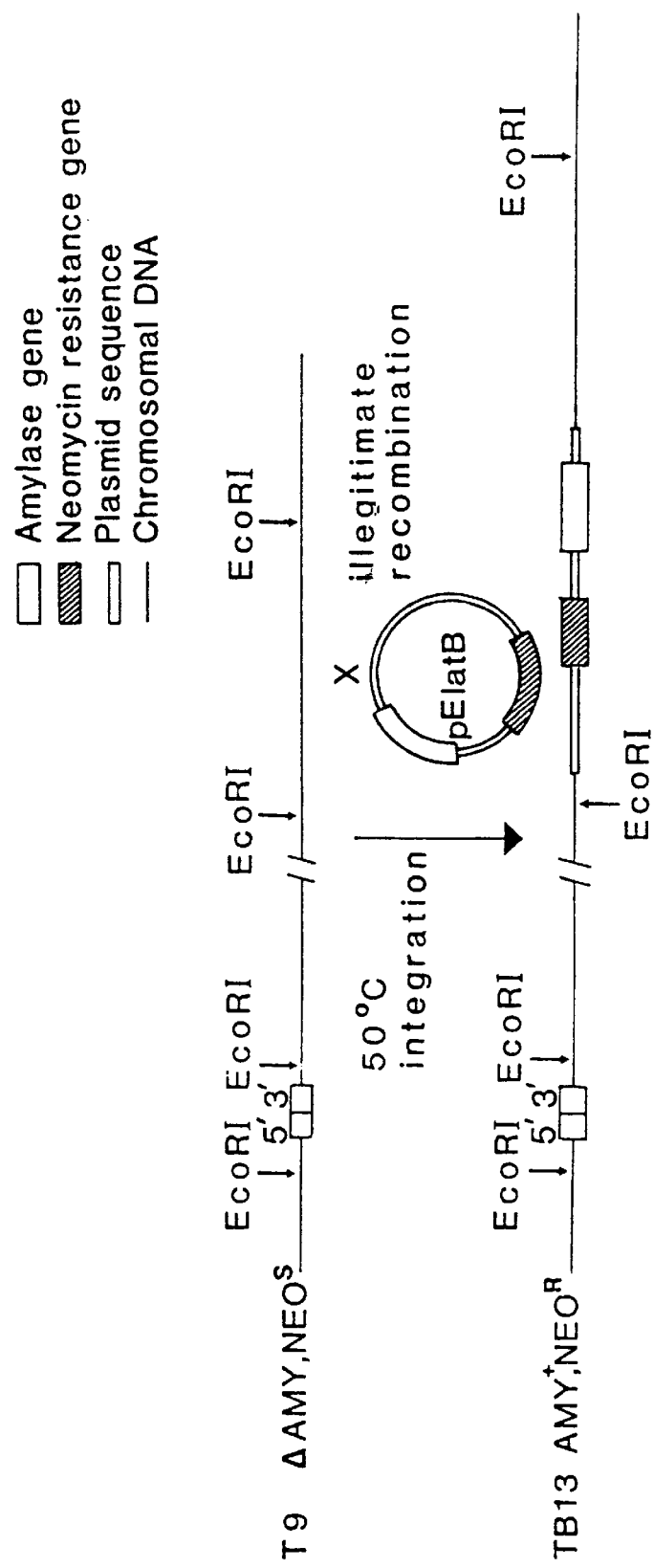

FIG. 9A illustrates the integration of plasmid pE1atB into the chromosome of B. licheniformis strain T9 resulting in B. licheniformis strain TB13.

Figure 9B:
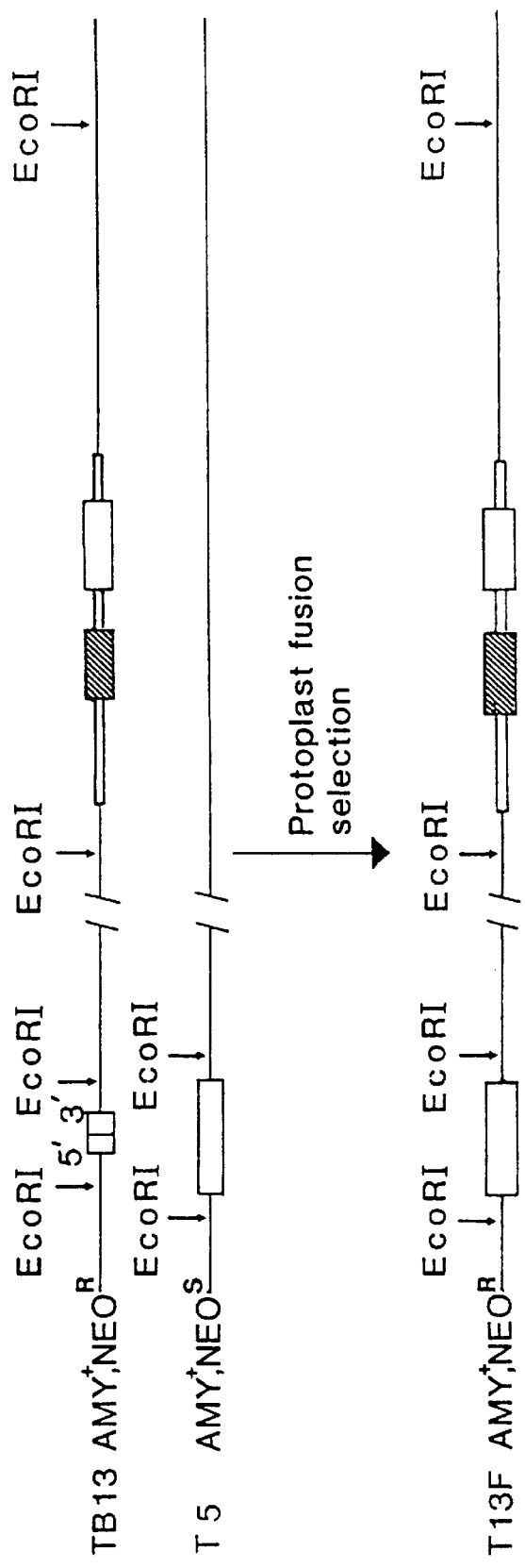

FIG. 9B illustrates the chromosomal recombination of the B. licheniformis strains TB13 and T5 upon protoplast fusion of these strains, resulting in B. licheniformis strain T13F.

Figure 10:
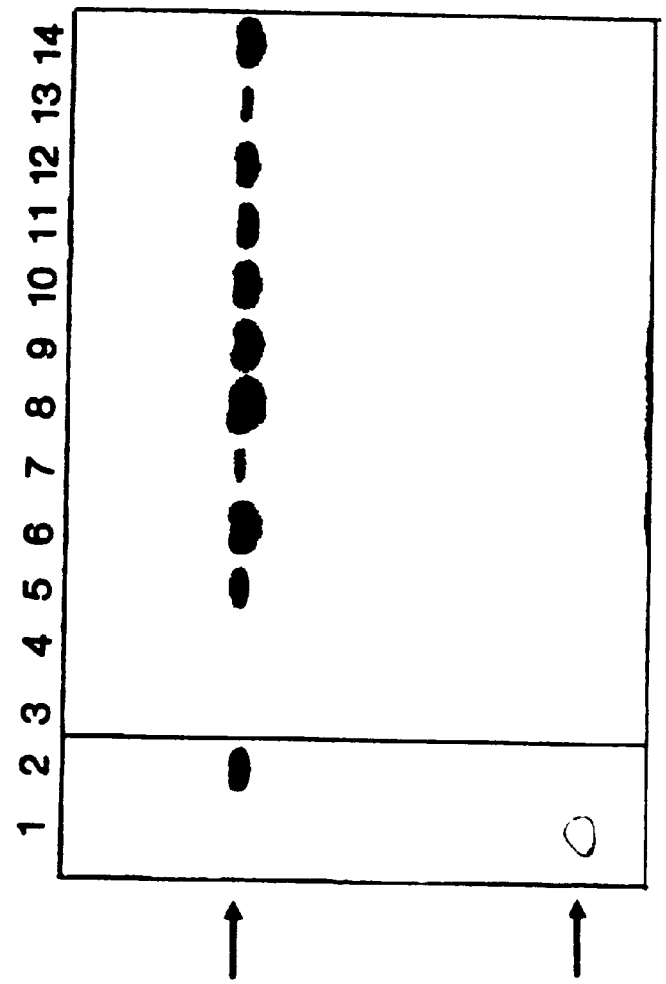

FIG. 10 shows a chromosomal analysis of nine different colonies isolated from a fermentation of strain T13F as described in Example 11. Isolated chromosomal DNA was digested with EcoRI separated on 0.8% agarose gels and blotted onto nitrocellulose. Hybridization of the blot was performed with $^{32}$P-labeled nick-translated pE1atB DNA. The figure shows an autoradiograph. The upper arrow indicates the position where an EcoRI DNA fragment of about 15 kb migrates which contains the entire pE1atB sequence that was integrated into the chromosome on a location not adjacent to the original α-amylase gene, as depicted for strain TB13 in FIG. 9A. The lower arrow indicates the position where an EcoRI DNA fragment of about 33 kb migrates which contains the entire α-amylase gene originally present in B. licheniformis strain T5 (see also FIG. 9B). The following DNA samples were analyzed:

Lane 1: B. licheniformis T5 DNA.
Lane 2: B. licheniformis TB13 DNA.
Lane 3: B. licheniformis T390 DNA.
Lane 4: DNA from a neomycin-sensitive derivative of B. licheniformis T390, isolated after fermentation, as described in Example 12.
Lane 5: B. licheniformis T13F DNA.
Lanes 6–14: DNA from nine different colonies isolated from a fermentation of strain T13F as described in Example 12.

DESCRIPTION OF THE SPECIFIC EMBODIMENTS

In accordance with the present invention, prokaryotic cells, and methods for their preparation, are provided in which two or more copies of a DNA sequence are stably integrated into the chromosome. A host cell comprising a DNA sequence encoding a polypeptide of interest is transformed with a DNA construct comprising said DNA sequence. Transformed cells in which the integrated DNA sequences are separated by endogenous chromosomal sequences from the gene to be amplified are then selected for. The endogenous intervening sequences are generally vital to the host cell. Loss of amplified sequences by homologous recombination will be lethal to the host cell. Thus, there will be selection pressure for cells carrying the amplified sequences without the necessity for using antibiotics or like selection means. Generally, the length of the intervening endogenous DNA sequences will be less than 10 kbp.

Figure 1A:
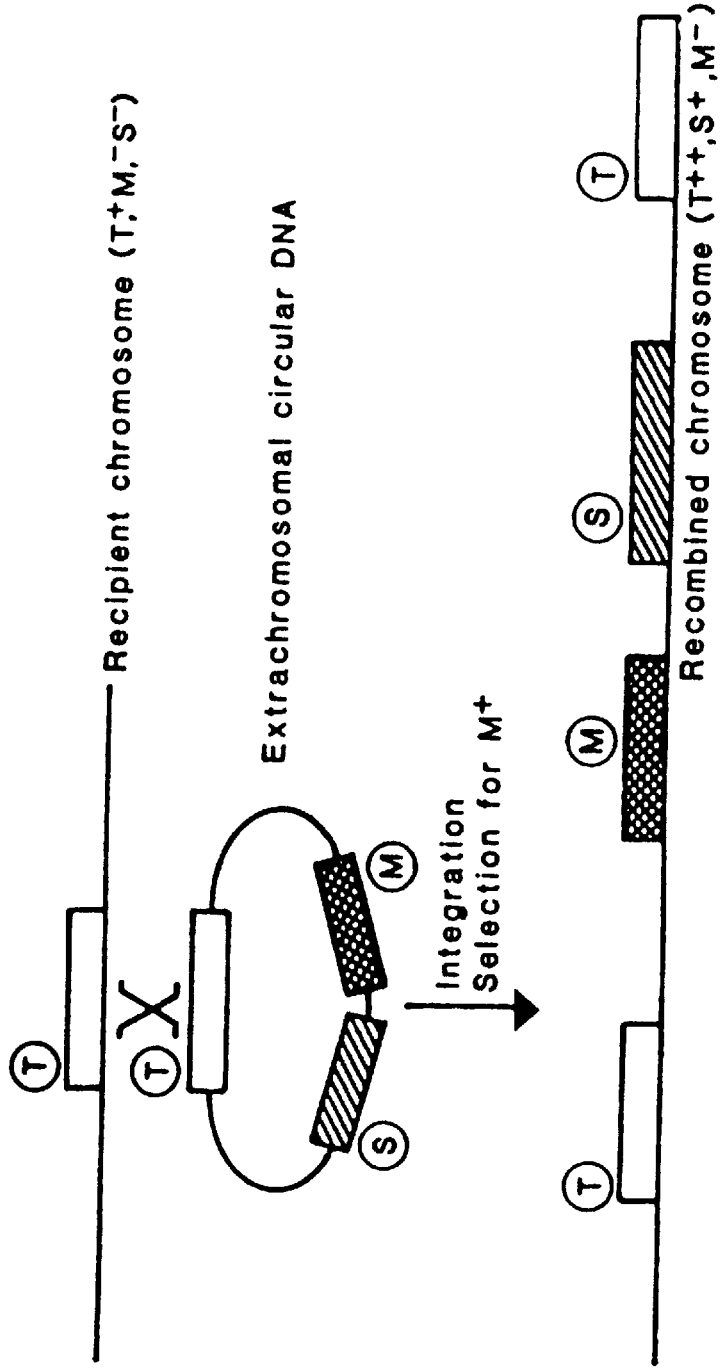
FIGS. 1A–D are schematic representations of four ways for integration of extrachromosomal DNA sequences into the chromosome of prokaryotic microorganisms.
Figure 1B:
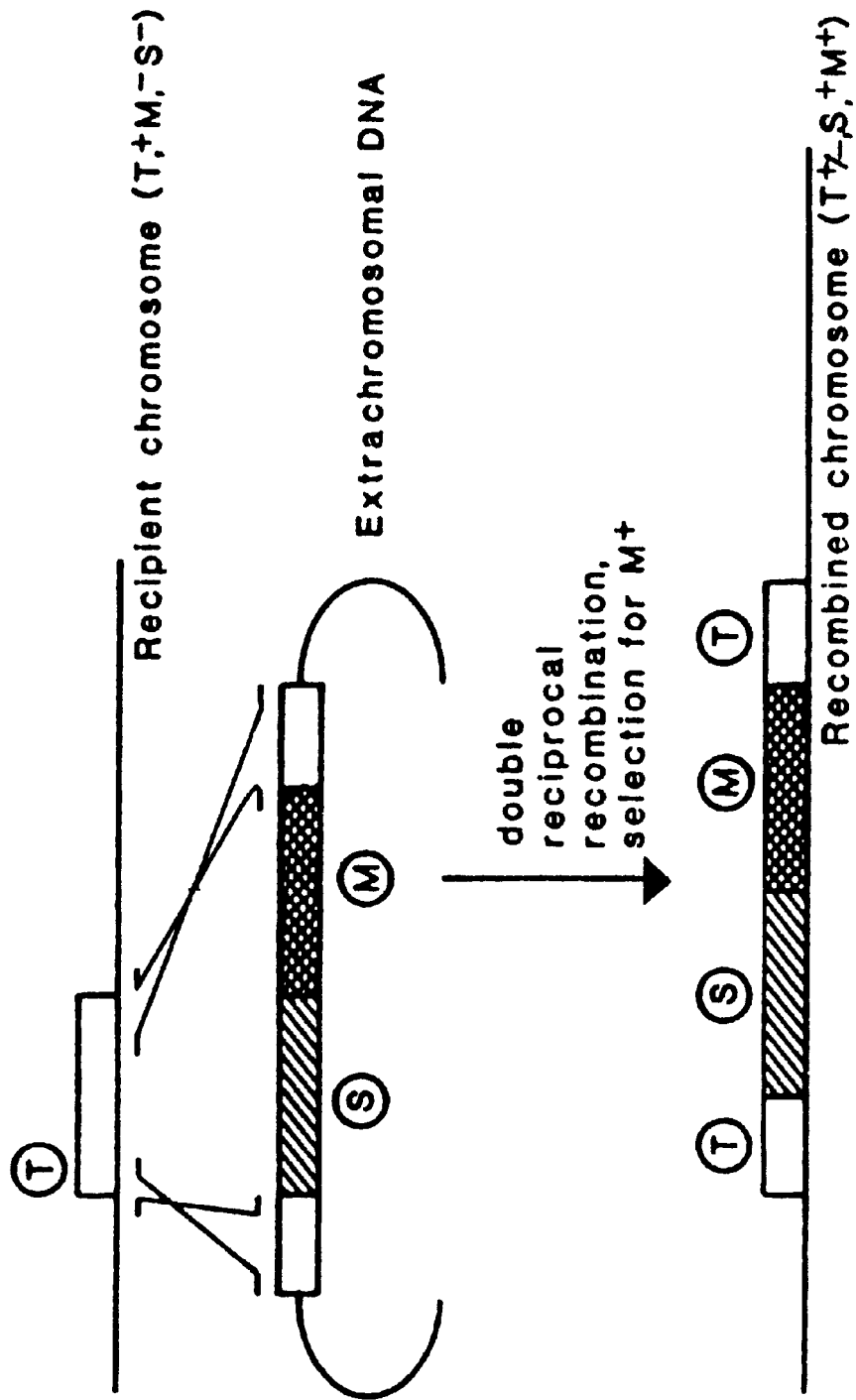
Figure 1C:
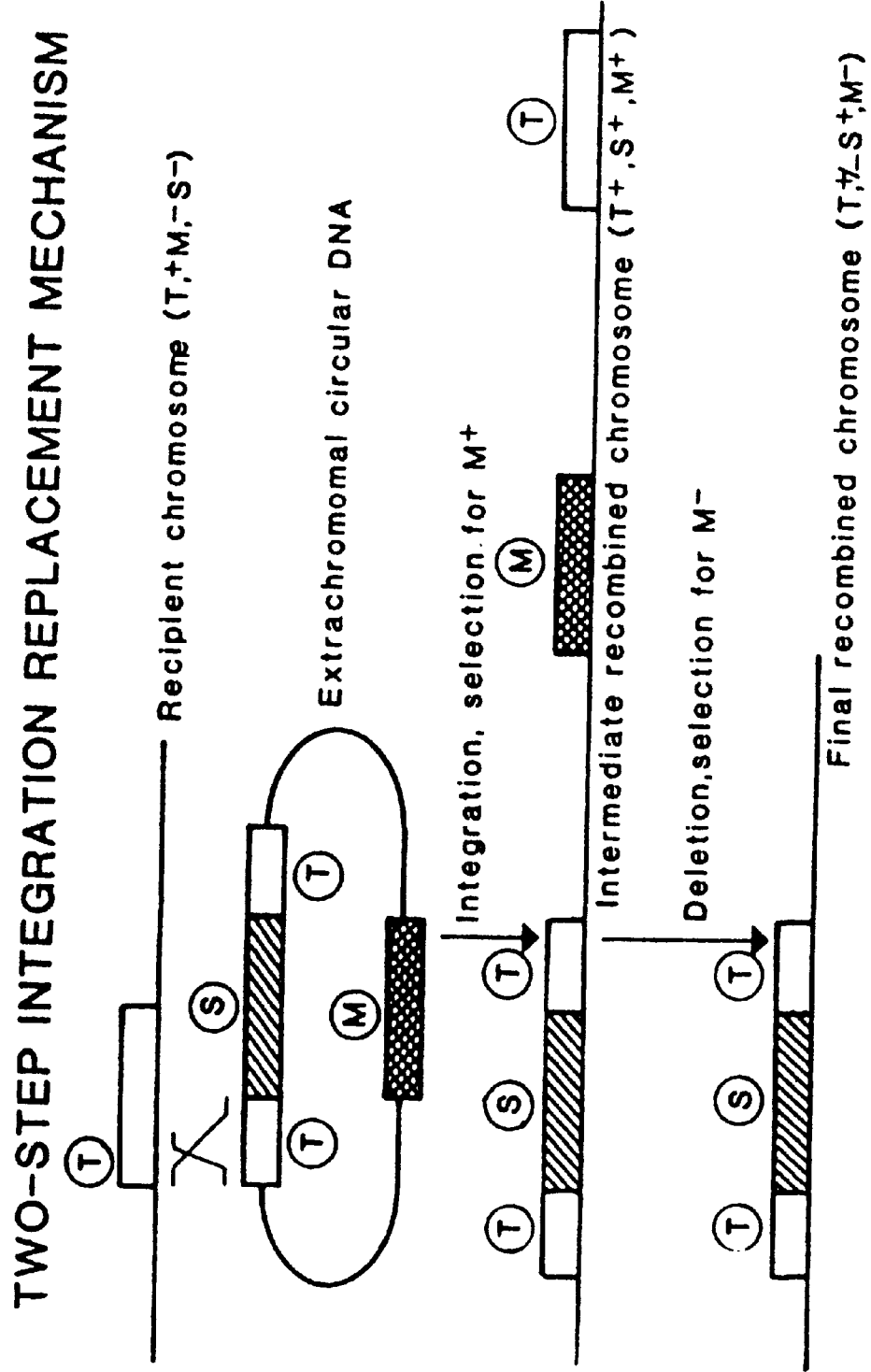
Figure 1D:
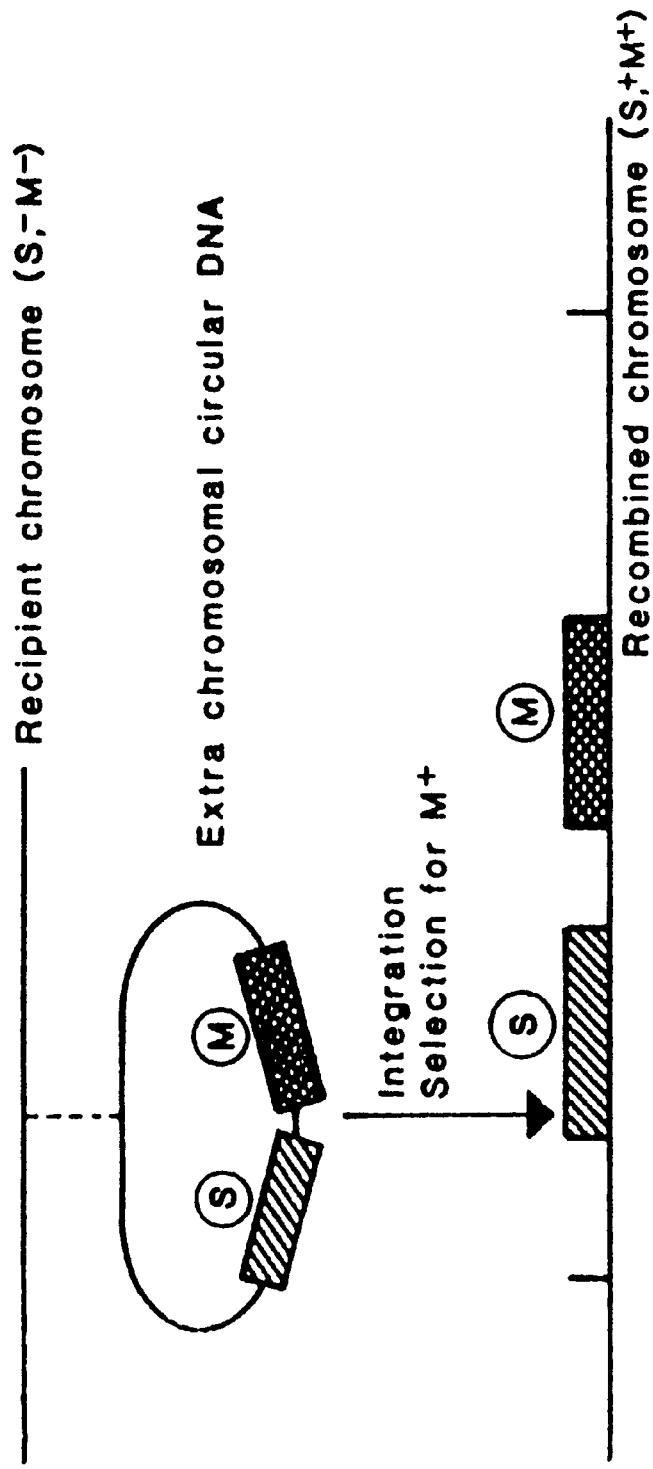

Several techniques can be used to obtain transformants having at least two copies of a gene of interest scattered in the transformant's chromosome. Examples of methods which can be used include those which avoid tandem integration, such as double reciprocal recombination as illustrated in FIGS. 1B and 2B. Several stretches of DNA sequences can be present in the vector molecules which are homologous to the host cell chromosome, especially when one or more copies of the gene to be amplified have already been introduced into the host cell. The vector molecule thus can include the DNA to be amplified; at least one target DNA sequence for recombination; and a marker DNA sequence.

Care has to be taken that only the desired recombined chromosomal arrangements are selected for. This can be achieved by using linear DNA molecules for recombination. The circular vector molecule to be integrated is cut with a restriction enzyme in the region homologous to the target sequence. In this way recombination and integration at this specific site can occur preferentially. In addition to being present in the vector molecule, the DNA sequence of interest can also be present in the host cell chromosome. The DNA sequence may be a DNA sequence encoding any structural gene which it is desired to amplify. The DNA sequence may be endogenous to the host organism, or may have been inserted into the host chromosome in a previous transformation step.

Target sequences for non-tandem gene amplification will preferably be chosen from among non-essential genes, for example in the case of Bacilli as host organisms, the genes encoding extracellular enzymes or genes involved in sporulation can be used as target sequences. Integration of DNA sequences in these genes will generally inactivate the gene. Loss of expression of the gene can then be monitored and used for the selection of the desired recombinant strains.

Other means for obtaining scattered gene transformants include the use of illegitimate recombination as illustrated in FIG. 2A. Isolation of tandem transformants can be avoided by selection using, for example, differential expression of a marker gene, for example a gene encoding antibiotic resistance, where sensitivity to the antibiotic is different in strains with tandem integration of the gene as opposed to non-tandem integration.

Scattered gene transformants can also be obtained by transforming first and second host cells which lack the structural gene of interest with a DNA construct comprising the structural gene, and a marker gene. First and second host cells in which the DNA sequence is present at different locations on the chromosome can then be selected and combined under fusing conditions to yield a transformed cell (acceptor strain) with at least two copies of the DNA sequence encoding the polypeptide of interest at scattered locations in its genome. For ease of selection the first host (donor host) can be killed prior to fusion. Depending upon the method of transformation used, a mixture of transformants having the genes of interest integrated in tandem array and those transformants having the genes of interest scattered in the chromosome, may be obtained. When a mixture of transformants is obtained, those containing scattered genes can be selected from the mixture by isolating chromosomal DNA from each individual transformant, and analyzing the isolated DNA with respect to the relative locations of the inserted genes by, for example, the method of Southern, J. Mol. Biol. (1975) 98:503–517 or other means known to those skilled in the art. Transformants having scattered integration of the genes of interest are thereby identified.

The gene(s) of interest may be any prokaryotic or eukaryotic gene. These genes may include bacterial genes, unicellular microorganism genes, mammalian genes, or the like. The structural genes may be prepared in a variety of ways, including synthesis, isolation from genomic DNA, preparation from cDNA, or combinations thereof. The various techniques of manipulation of the genes are well-known, and include restriction, digestion, resection, ligation, in vitro mutagenesis, primer repair, employing linkers and adapters, and the like. Thus, DNA sequences obtained from a host may be manipulated in a variety of ways, depending upon the requirements of the DNA construction. See Maniatis et al., Molecular Cloning, Cold Spring Harbor Laboratory, Cold Spring Harbor, N.Y., 1982.

The structural genes may express a variety of polypeptides or proteins, such as enzymes, hormones, lymphokines, surface proteins, blood proteins, structural proteins, immunoglobulins, or the like, from mammals, unicellular microorganisms, e.g., bacteria, fungi, such as yeast, or filamentous fungi, algae, protozoa, etc., plants, or other DNA source. Of particular interest are enzymes, more particularly proteases and amylases. Illustrative of such enzymes are serine and non-serine proteases including high alkaline serine proteases, α- and β-amylase, and the like. Preferably a polypeptide of interest (e.g., an enzyme) is a serine protease whose coding sequence has at least 70% homology with the nucleic acid that encodes the amino acid sequence corresponding to residues I to 269 of SEQ ID NO: 2. A preferred source for a serine protease is Bacillus novo species PB92, and for an alpha amylase is B. licheniformis strain T5, as well as variants and mutants of these strains.

The gene that forms part of the suitable vector can be obtained by methods generally known in the art. Generally, the method comprises preparing a genomic library from the organism expressing the polypeptide of interest. The genomic library is conveniently prepared for example by ligating DNA fragments of the donor strain into a suitable vector.

By the term "suitable vector" is meant a DNA construct comprising a structural gene encoding a protein or polypeptide of interest, in particular an enzyme. The structural gene is joined in proper orientation to control regions such as a promoter sequence, a sequence forming the ribosome binding site and sequences controlling termination of transcription and translation of the structural gene, which control regions are functional in the host cell. Where the host cell has transformation and integration frequencies which are too low to permit direct selection for integration without intermediate isolation of plasmid containing cells, such as industrial Bacillus strains, the vector can additionally comprise an origin of replication that is capable of replicating autonomously in the host cell.

Where the gene is obtained from a donor cell which has transcriptional and translational initiation and termination regulatory signals which are recognized by the host prokaryotic cell strain, it will usually be convenient to maintain the original regulatory sequences of the structural gene. In addition, the transcriptional initiation region may provide for constitutive or inducible expression, so that in appropriate situations, the host may be grown to high density before high levels of expression of the structural genes of interest are obtained.

Where the structural gene is from a source whose regulatory signals are not recognized by the host cell, it will be necessary to obtain regulatory regions recognized by the host cell and to insert the structural gene between the initiation and termination regulatory signals. In some instances the exogenous structural gene with its own stop codon(s) may be inserted in reading frame behind the N-terminus codons of an endogenous structural gene which retains its natural regulatory signals.

It is desirable that the expression product be secreted. Where the expression product is naturally secreted and the leader signals and processing signal(s) are recognized by the host cell, this will entail no difficulty. However, where the product is not secreted because the host cell does not recognize the secretory leader signals and/or processing signal(s), or the signals are not functional to a satisfactory degree in the host cell, then it may be necessary to isolate or synthesize DNA sequences coding for the secretory leader signals and processing signal(s) of a host cell polypeptide and join them in proper reading frame to the 5'-end of the structural gene.

The vector may additionally include a marker gene conferring resistance to an antibiotic to which the host strain is sensitive. The marker gene, when used in chromosomal integration of the vector, has to fulfill the demand that survival selection is possible even if only one or a few copies of the marker gene are present in the host strain. By marker is intended a structural gene capable of expression in a host, which provides for survival selection. By "survival selection" is intended imparting prototrophy to an auxotrophic host, biocide or viral resistance. For prototrophy, various genes may be employed, such as leu, his, trp, or the like. For biocide resistance this may include resistance to antibiotics, e.g., neo, cam, tet, tun, kan, or the like. Other markers include resistance to heavy metals, immunity, and the like. The various DNA sequences may be derived from diverse sources and joined together to provide for a vector which includes one or more convenient, preferably unique, restriction sites to allow for insertion or substitution of the structural genes at such sites or in place of lost fragments to provide the plasmid construct.

Selection for chromosomal integration may be aided by using a plasmid with an origin of replication having a mutation which makes its functioning temperature-sensitive in the host cell. See, for example, Ehrlich, *Proc. Natl. Acad. Sci. USA* (1978) 75:1433.

Once the plasmid construct has been prepared, it may now be cloned in an appropriate cloning host. Any host may be used which is convenient, is readily transformable, and allows for replication of the plasmid construct and transfer to the host cell. A large number of strains are available which have a high efficiency of transformation and are usually auxotrophic and/or antibiotic sensitive. Where the host cell is an industrial Bacillus strain, the use of the same organism as the host cell for cloning of the plasmid construct has many advantages in that it permits the use of a single replication system as well as the same marker for survival selection in both the cloning host and the host strain. See, for example, European application EP-A-0134048, which disclosure is incorporated herein by reference.

The plasmid construct may be introduced into the cloning host in accordance with conventional techniques, such as transformation, employing calcium precipitated DNA, conjugation, or other convenient technique. The cloning host may then be grown in an appropriate nutrient medium, under selective conditions to select for a host containing the plasmid construct. For auxotrophic hosts, the nutrient medium is deficient in the required nutrient, while for biocide resistance, e.g., antibiotic resistance, a cytotoxic amount of the biocide(s) is employed in the nutrient medium.

Various host cells may be employed. These include *E. coli*, Bacillus strains, especially *B. subtilis*, Pseudomonas, and Streptomyces. In choosing a host cell, various factors are taken into account, including factors which can affect expression of the gene to be amplified and production of the desired product. Thus it is desirable to use a host cell in which there is recognition of regulatory signals; ease of secretion; reduced degradation of the desired product, etc. A preferred host cell already produces the polypeptide of interest, and may be either a wild type organism or a mutant organism. The host cell can also be a mutant of an organism which produces the polypeptide of interest which itself, however, is a non-producer. Where the polypeptide of interest is a protease or an amylase, preferred strains include Bacillus novo species PB92 30 and *B. licheniformis* strain T5 respectively, as well as mutants and variants of these strains.

In addition, host strains may be employed which have the desired traits of an industrial strain. Examples or strains which may be employed include strains used for the industrial production of enzymes such as: *B. licheniformis, B. amyloliquefaciens* and alkalophilic bacilli. The industrial strains are chosen from organisms which may be isolated in the soil or available from depositories or other sources or obtained by modification of such strains. The industrial strains are highly robust and stable. Furthermore, such strains are resistant to phage infection and to genetic exchange, that is introduction of DNA by conventional transformation procedures. The conventional industrial strains are also prototrophic, in order to avoid adding expensive amino acids to the nutrient medium. Other characteristics of industrial stains are their high productivity until the end of the fermentation, which can be as long as a week, stable cell concentration upon exhaustion of the broth, and high productivity, usually at least 5 g/l (0.5% w/v) of a specific secreted protein.

Transformation of the host cells preferably involves the use of protoplasts prepared from the host strain. Protoplasts generally are prepared from the host cells in accordance with conventional ways, e.g, lysozyme or zymolyase treatment, and the protoplasts carefully suspended in an appropriate medium having proper osmolality for maintaining the integrity of the protoplast. For industrial Bacillus strains, methods for preparing protoplasts are described in European Application No. EP-A-0134048, which disclosure is incorporated herein by reference. Where the host strain is an alkalophilic Bacillus strain, protoplasts may conveniently be prepared at alkaline pH, preferably about pH 8.0. This procedure is disclosed in European Application No. EP-A-87200358.7, which disclosure is incorporated herein by reference.

The host cell can be transformed by combining the plasmid construct or a cloning host protoplast with the host cell protoplast in the presence of an appropriate fusogen. Any fusogen may be employed which provides the desired degree of efficiency. For the most part, polyethylene glycol is found to provide high efficiency of fusion with great convenience. After a short time, the fusogen mixture is replaced with an appropriate nutrient medium and cells regenerated in a selective medium, conveniently by plating on an agar plate.

Transformants obtained by combining a host cell with a suitable DNA construct can contain a DNA construct or part thereof either directly as an integral part of the chromosome or as a free vector molecule when the DNA construct contains an origin of replication functional in the host cell. To select for transformants which have the DNA construct integrated into the chromosome, a plasmid containing a temperature-sensitive origin or replication can be used. Transformants are grown in a selective medium at the permissive temperature, then shifted to a non-permissive temperature. Colonies expressing the marker gene at the non-permissive temperature are then isolated and cultured in selective medium at the permissive temperature. Plasmid absence can be verified, for example by isolating total DNA from the colonies and electrophoresing on an agarose gel or by demonstrating lack of ability of the transformants to transform competent cells. Determination of the way in which integration into the chromosome has taken place can be by analysis of the chromosomal DNA by, for example, the method of Southern, supra., or other methods known to those skilled in the art.

When there is a differential sensitivity to the selective agent between transformants containing additional copies of the marker gene in a tandem array as compared to those in which the marker gene is incorporated at scattered locations in the host genome, transformants can conveniently be grown in medium containing the appropriate concentration of selective agent to select for transformants with non-tandem integration.

Another means of obtaining transformants with scattered integration of copies of the DNA sequence of interest is to use a protoplast prepared from an homologous donor cell, containing at least one copy of the DNA sequence of interest at a location on its chromosome different from that of the recipient host cell. The homologous donor cell can be prepared, for example, by transforming a cell which does not contain the structural gene of interest with a vector comprising the structural gene. Integration of the DNA sequence into the donor cell chromosome can be facilitated by using a plasmid containing a temperature-sensitive origin of replication and growing transformants under selective conditions first at the permissive temperature and then at the non-permissive temperature as described above, then isolating colonies expressing the marker gene.

Following verification of the absence of plasmid DNA, the chromosomal DNA can be isolated and analyzed according to the method of Southern, supra, by hybridizing with a probe labeled with, for example, $^{32}P$ or biotinylated nucleotides. The probe may be cDNA encoding the polypeptide of interest or fragments thereof as well as DNA constructs or fragments thereof comprising the DNA sequence of interest, for example a vector. Transformants containing the gene of interest at an alternate location as compared to that of the gene donor strain can then be used as an homologous donor cell. The recipient strain host is preferably the same as the strain used as the source of the DNA sequence of interest, or a strain in which the DNA sequence of interest is located at a different region of the chromosome than in the transformed donor cell.

To aid in selection, the donor cell preferably is killed with a cytotoxic agent prior to or during protoplast formation. Various agents may be employed to kill the donor cell, including antibiotics, but iodoacetamide is found to be convenient, efficient, and does not interfere with the subsequent fusion. When dead cloning host protoplasts are used, the ratio of the dead protoplast to the acceptor strain host will be preferably at least about 1:1 and an excess of the dead protoplast may be employed.

Following fusion of the dead donor cell protoplast and the recipient host cell protoplast, transformants can be selected by means of the marker gene. DNA can then be isolated and analyzed as described above to identify transformants in which more than one copy of the gene of interest has been incorporated into the genome and are separated by endogenous chromosomal sequences.

Scattered two-gene transformants are then screened in appropriate ways for detection of increased expression of the polypeptide of interest. Various techniques may be employed, particularly where enzymes are involved which have well established methods of detection. Alternatively, where enzymes are not involved or there is no available detection system, bioassays, antibodies, restriction analysis, or DNA or RNA hybridization can be employed for screening the clones to determine the presence of the plasmid construct and expression of the structural gene of interest.

The host cell containing the chromosomally integrated plasmid constructs or fragments thereof is then grown in a nutrient medium under conventional fermenting conditions. The fermenting may be continued until the broth is exhausted. Where the product has been secreted, the product may be isolated from the broth by conventional techniques, e.g., extraction, chromatography, electrophoresis, or the like. Where the product is retained in the cytoplasm, the cells may be harvested by centrifugation, filtration, etc., lysed by mechanical shearing detergent, lysozyme, or other techniques and the product isolated as described previously.

The following examples are offered by way of illustration and not by way of limitation.

EXPERIMENTAL

Example 1

Preparation of a Genomic DNA Library from Alkalophilic Bacillus novo sp. PB92 and Isolation of the Serine Protease Gene Chromosomal DNA was isolated from Bacillus novo sp. PB92 (deposited at the American Type Culture Collection (ATCC) American Type Culture Collection (ATCC), 10801 University Blvd., Manassas, Va. 20110-2209 on May 8, 1987 under ATCC Accession Number 31408 and deposited under No. OR-60 with Laboratorium voor Microbiologie, Technical University of Delft, the Netherlands, see U.S. Pat. No. Re. 30,602) according to the procedure described by Saito-Miuva, *Biochim. Biophys. Acta* (1963) 72:619–632. The DNA was partially digested with the restriction enzyme Sau3A and ligated into the BamHI site of plasmid pUB110 (Gryczan et al., *J. Bacteriol.* (1978) 134:318–329). pUB110 plasmid DNA was prepared as described by Birnboim and Doly (*Nucleic Acids Res.* (1979) 7:1513–1523).

The ligation mixture was transformed into *B. subtilis* 1A40 (Bacillus Genetic Stock Center) according to the method of Spizizen et al., *J. Bacteriol.* (1961) 81:741–746, using 0.6–1 µg DNA per ml of competent cells. Cells from the transformation mixture were plated on minimal plates containing: 2.8% $K_2HPO_4$, 1.2% $KH_2PO_4$, 0.4% $(NH_4)_2SO_4$, 0.2% tri-Na-citrate-$2H_2O$, 0.04% $MgSO_4 \cdot 7H_2O$, 0.00005% $MnSO_4 \cdot 4H_2O$, 0.4% L-glutamic acid, 0.5% glucose, 0.02% casamino acids, 50 µg/ml tryptophan, 20 µg/ml methionine, 20 µg/ml lysine, 20 µg/ml neomycin, 0.4% casein and 1.5% agar. After overnight incubation of the plates at 37° C., one out of 50,000 neomycin resistant colonies showed increased protease production, as determined by increased precipitation of a halo of casein cleavage products around the colony in the agar plate. Plasmid DNA was isolated from this colony according to the method described by Birnboim and Doly, *Nucleic Acids Res.* (1979) 7:1513–1523, and named pM58.

Example 2

Expression of the PB92 Serine Protease Gene

*Bacillus subtilis* 1A40 containing pM58 was grown in minimal medium (Spizizen et al., *Proc. Natl. Acad. Sci. USA* (1958) 441:1072–1078) to which had been added 0.02% casamino acids, 50 µg/ml tryptophan, 20 µg/ml methionine, 20 µg/ml lysine and 20 µg/ml neomycin. After 24 hours, the culture was centrifuged and the supernatant assayed for protease activity using dimethyl casein as substrate (Lin et al., *J. Biol. Chem.* (1969) 244:789–793. A control culture of *B. subtilis* 1A40 containing the plasmid pUB110 showed less than 1/60 of the protease activity shown by the pM58 transformed culture. Protease activity was completely inhibited by treatment with 1 mM phenylsulfonyl fluoride (PMSF), but not by treatment with 20 mM EDTA.

Aliquots of the above described supernatants were analyzed on protein gels according to the method of Laemmli, *Nature* (1970) 227:680. Samples for analysis on these gels were prepared by treatment of the supernatants with 5% trichloroacetic acid (TCA). Following centrifugation of the sample, the pellet of precipitated protein was washed twice with acetone then dissolved in 40 µl sample buffer (0.5 M Tris/HCl, pH 7.5, 10% v/v 2-mercaptoethanol, 50% v/v glycerol and 0.05% Bromophenol Blue) by boiling for 10 minutes. Culture supernatant samples were then analyzed by electrophoresis. Three different *B. subtilis* 1A40 strains were used: a strain containing pUB110; pM58 and no plasmid, and Bacillus PB92 protease as a control. After electrophoresis, the gels were stained using Coomassie Brilliant Blue and destained. The sample from *B. subtilis* strain 1A40 containing pM58 contained a 31 kD protein, which comigrates with Bacillus PB92 protease. This protein was not detected on the control lane of strain *B. subtilis* 1A40 containing pUB110.

All serine proteases have similar molecular weights. The cloned serine protease of Bacillus PB92 therefore was differentiated from known serine proteases (*B. subtilis* subtilisin, Carlsberg subtilisin), by transformation of pM58 and pUB110 to the protease negative *B. subtilis* strain DB104 (Doi, *J. Bacteriol.* (1984) 160:442–444) and analysis of the extracellular proteases produced. The obtained transformants were grown in minimal medium (Spizizen et al., *Proc. Natl. Acad. Sci. USA* (1958) 44:1072–1078) containing 0.02% casamino acids, 50 µg/ml histidine and 20 µg/ml neomycin. After 24 hours, samples were taken, centrifuged and without pretreatment analyzed on histidine/MOPS gels containing 75 mM KOH, 40 mM histidine, 100 mM MOPS (3-(N-morpholino)-propanesulfonic acid), pH 7.5 and 5% polyacrylamide. Electrophoresis buffer contained 40 mM histidine, 100 mM MOPS, pH 6.6. Samples were run in the direction of the cathode. Protease bands were detected with Agfa Pan 100 Professional films (Zuidweg et al., *Biotechnol. and Bioengin.* (1972) 14:685–714). These results are shown in FIG. 3. As shown in FIG. 4, pM58 harbors the gene encoding Bacillus PB92 protease.

Example 3

Sequencing of the Bacillus novo species PB92 Serine Protease Gene

The entire sequence of a BalI-HpaI fragment of pM58 was determined by the method of Sanger, *Proc. Natl. Acad. Sci. USA* (1977) 74:6463. Restriction fragments of pM58 (see FIG. 4) were cloned in phage M13 vectors mp10, mp11 and mp18 (Messing et al., *Nucleic Acids Res.* (1981) 9:309–321. Insertions of pM58 fragments were screened by plaque hybridization. After sequencing, ten oligonucleotides located at regular distances on the gene were made and sequencing was repeated, confirming the sequence shown in FIGS. 5A–F.

Example 4

Construction of Serine Protease Containing Plasmid pMAX-4

To construct plasmid pUCN710 (FIG. 6A) UB110 was digested with TaqI and PvuII. The fragment containing the gene conferring neomycin resistance was purified on low melting agarose and made blunt with Klenow polymerase and NTP's (Maniatis, *Molecular Cloning: A Laboratory Manual*, Cold Spring Harbor 1982). Plasmid pUC7 (Vieira et al., Gene (1982) 19:259–268) was linearized with SalI and made blunt as described above. Both fragments were ligated with T4 ligase (Maniatis) and transformed to JM103. Selection took place on 2xTY plate (1.6% w/v Bacto-trypton, 1% w/v yeast extract, 0.5% NaCl) containing 50 μg/ml ampicillin and 10 μg/ml neomycin. The resulting plasmid, named pUCN710, was digested with BamHI. The plasmid pE194 (Jordanescu, Plasmid (1978) 1:468–479) was digested with BclI. The fragments from both digestions were ligated with T4 ligase and transformed to *B. subtilis* 1A40. Selection took place on minimal plates containing 20 μg/ml neomycin (see Example 1). The plasmid obtained, pE194-neo (FIG. 6A), contains the neomycin gene and a temperature sensitive origin of replication.

Subcloning of the protease gene in integration vector pE194-neo was performed as follows: pM58 (see Example 1) was digested with HpaI, BalI and BglII. Plasmid pE194-neo was digested with HpaI. These fragments were ligated with T4 ligase and transformed to *B. subtilis* 1A40. Transformants were selected based upon neomycin resistance and an increase in protease production, as judged by case in cleavage products precipitation (halo formation, see Example 1). Plasmid pMAX-4 was obtained, the structure of which was confirmed by restriction enzyme analysis (see FIG. 6B).

Example 5

Protoplast Transformation of Bacillus novo strain PB92 by pMAX-4

Bacillus strain PB92 was grown overnight in 100 ml NBSG-X medium (Thorne et al., *J. Bacteriol.* (1966) 91:1012–1020). The culture was centrifuged for 10 minutes at 4,500 rpm in a Sorvall model GSA rotor. Protoplasts were prepared by incubating the bacilli for one hour at 37° C. in 10 ml Alkaline Holding Medium (AHM) containing 0.5 M sucrose, 0.02 M $MgCl_2$ and 0.02 M Tris/maleate, pH 8.0, in sterile water to which 0.4 mg/ml lysozyme was added. The protoplasts were pelleted (10 minutes at 4,500 rpm), resuspended in 5 ml $AHM^+$ pH 8.0 buffer (AHM buffer to which 3.5% w/v Bacto Penassay Broth and 0.04% w/v Albumine Merieux had been added) mixed, then pelleted as above.

After being resuspended in 5.0 ml of alkaline holding medium, 0.5 ml of this suspension of protoplasts were mixed with 5 μl of demineralized water containing 1 μg of plasmid DNA and incubated for 2 minutes in the presence of 30% w/v polyethylene glycol 8,000, pH 8.0. After 1:3 dilution with AHM+pH 8.0 medium and centrifugation, the pellet was resuspended in a small volume (1 ml) of $AHM^+$ and incubated for 2–3 hours. One hundred microliter aliquots were plated on freshly prepared regeneration plates containing 0.5 M Na succinate/HCl pH 8.0, 1.5% w/v agar, 0.5% w/v casamino acids, 0.5% w/v yeast extract, 0.031 M phosphate buffer pH 8.0, 0.5% w/v glucose, 0.02 M $MgCl_2$ and 0.02% w/v Albumine Merieux. These plates also contained 1 mg/ml neomycin for selection. After incubation at 37° C. for at least 72 hours, the colonies were replica-plated onto heart infusion agar plates containing 20 μg/ml neomycin.

Example 6

Integration of pMAX-4 in the Bacillus Strain PB92 Chromosome

A transformant of Bacillus PB92 containing plasmid pMAX-4, was incubated in Tryptone Soya Broth (TSB) containing either 1 μg/ml or 20 μg/ml neomycin for 24 hrs at 37° C. Two ml portions of the cell suspensions were then diluted in 100 ml of TSB containing 1 μg/ml or 20 μg/ml neomycin, respectively, and incubated for 24 hrs at 50° C. After 24 hrs 5 ml samples of both cultures were diluted again, as described above, and incubated for 24 hrs at 50° C., again in the presence of 1 μg/ml or 20 μg/ml neomycin, respectively. The last procedure was repeated once more. The cell suspensions were then diluted 100-fold and plated on Heart Infusion (HI) agar plates containing 1 μg/ml neomycin for the samples from the flasks containing 1 μg/ml neomycin, and 20 μg/ml neomycin for the samples from the flasks containing 20 μg/ml neomycin. The plates were incubated for 16 hrs at 50° C. Neomycin-resistant colonies were isolated and cultured in 10 ml TSB medium containing 1 μg/ml neomycin for 16 hrs at 37° C. From these cultures total DNA was isolated (Holmes et al., *Anal. Biochem.* (1981) 114:193–197). Plasmid absence was verified by DNA electrophoresis on agarose gel. Absence of plasmid DNA from samples in which plasmid DNA was not detectable was confirmed by transformation of total DNA to *B. subtilis* 1A40. Samples lacking the ability to transform *B. subtilis* 1A40 were considered plasmid-free.

To check whether and in what way integration of pMAX-4 in the chromosome took place, chromosomal DNA was isolated, digested with HindIII, run on 0.5% DNA agarose gels and blotted to nitrocellulose (Southern, *J. Mol. Biol.* (1975) 98:503–517), and hybridized with $^{32}$P-labeled nick-translated pM58 (Maniatis, *Molecular Cloning: A Laboratory Manual*, 1982, Cold Spring Harbor). The result of this analysis is shown in FIG. 7A.

Selection at 1 μg/ml neomycin resulted in protease genes tandemly located in the chromosome and separated by plasmid sequences (strain PBT109) as a result of homologous recombination (Campbell-type mechanism). In an accumulation of 30 independently isolated integrants, selection was performed at 1 μg/ml neomycin. One integrant was isolated which contained the plasmid pMAX-4 on a random location in the chromosome as a result of an illegitimate recombination (strain PBT122). Selection at 20 μg/ml neomycin resulted in a copy of a plasmid pMAX-4 on a random location in the chromosome as a result of an illegitimate-type recombination. The latter strain was named PBT108. The genetic organization of strains PBT109 and 108 are depicted in FIGS. 7B and 7C, respectively. Chromosomal analysis showed that integration in PBT122 and PBT108 occurred on different locations in the chromosome.

Example 7

Stability of Duplicated Protease Genes in Strains PBT108 and PBT109

One hundred ml of production medium (1% starch, 4% lactose, 0.87% $K_2HPO_4$, 0.5% yeast extract, 0.5% $(NH_4)_2HPO_4$, 0.2% Tri Na citrate-$2H_2O$, 0.05% $MgSO_4.7H_2O$, 0.07% $CaCl_2$, 0.068% $FeSO_4.7H_2O$ and antifoam 1 ml/l) without neomycin was inoculated with 0.2 ml of an overnight TSB culture (37° C.) of strain PBT108 or PBT109 in 500 ml shake flasks. After incubation for 44 hrs at 37° C. under constant aeration the culture was tested for neomycin-resistant colonies and for protease activity.

Both strains PBT108 and PBT109 were also tested in Eschweiler fermenters into the same production medium to check the effect of upscaling to 10 l. The results of the fermentation experiments are summarized in the following table.

TABLE 1

| Strain | Relative Production of Protease* | Percent of Neomycin-Resistant Cells After Fermentation |
|---|---|---|
| Control (PB92) | 100% | — |
| PBT108 | 120% | 100% |
| PBT109 | 115–120% | 75–97% |

*Protease activity was assayed using dimethylcasein as substrate as described by Lin et al., J. Biol. Chem. (1969) 244:789–793.

Analysis of colonies derived from the Eschweiler fermentation of PBT109 after 2 days of culturing, showed that 3–25% of these colonies produced at the level of a strain containing only a single protease gene. These same colonies were neomycin-sensitive due to excission of the pMAX-4 sequence by homologous recombination. However, analysis of the colonies derived from the strain PBT108 fermentation experiment showed that these cells were all neomycin-resistant. One hundred of these neomycin-resistant colonies were taken at random and individually tested for protease production potential, to determine whether they contained one or two productive protease genes. All 100 individually tested colonies produced at the level of a strain containing two genes, showing that the two randomly integrated protease genes in PBT108 are stably maintained under the fermentation conditions used.

Example 8

Construction of Integration Vector pE1atB

Plasmid pGB34, described in EP-A-0134048, was digested with the restriction enzymes BclI, BglI and BglII. The restriction fragments obtained were blunt-ended with Klenow polymerase, then were ligated into the HpaI site of pE194neo (see Example 6). Plasmid pE194neo DNA was isolated as described by Birnboim and Doly, *Nucl. Acids Res.* (1979) 7:1513–1523.

The ligation mixture was transformed into *B. subtilis* 1-A40, according to the method of Spizinen et al., *J. Bacteriol.* (1961) 81:741–746, using 0.5 to 1 μg DNA/ml of competent cells. Cells from the transformation mixture were plated on minimal plates containing 2.8% $K_2HPO_4$, 1.2% $KH_2PO_4$, 0.4% $(NH_4)_2SO_4$, 0.2% Tri Na citrate.$2H_2O$, 0.04% $MgSO_4.7H_2O$, 0.00005% $MnSO_4.4H_2O$, 0.4% glutamic acid, 0.5% glucose, 0.02% casamino acids, 50 μg/ml tryptophan, 20 μg/ml methionine, 20 μg/ml lysine, 20 μg/ml neomycin, 0.4% casein, 0.5% starch and 1.5% agar.

DNA of α-amylase producing colonies was isolated as described by Birnboim and Doly and checked with restriction enzymes. From one of these transformants plasmid pElatB, see FIG. 8, was isolated.

Example 9

Transformation of the α-amylase Negative Strain Bacillus licheniformis T9 with pElatB Transformation of *B. licheniformis* strain T9 was carried out as described in EP-A-0253455 with the exception that the entire procedure was performed at 30° C. instead of at 37° C. Selection for transformants was carried out on minimal plates containing 20 μg/ml neomycin. All transformants produced amylase. Restriction enzyme analysis performed on DNA prepared as described by Birnboim and Doly showed that the transformants all contained pElatB.

Example 10

Integration of pElatB into the *B. licheniformis* T9 Chromosome

*Bacillus licheniformis* strain T9 containing plasmid pElatB, was inoculated in Tryptone Soya Broth (TSB) containing 20 μg/ml neomycin and incubated for 16 hours at 30° C. A 5 ml portion of the cell suspension was then diluted in 100 ml of the same medium and incubated at 50° C. for 24 hours.

This procedure was repeated once. The cell suspension was then diluted 100-fold and plated on Heart Infusion Agar plates containing 10 μg/ml neomycin. After 40 hours of incubation at 50° C., neomycin resistant colonies were isolated and cultured in 10 ml TSB medium, containing 10 μg/ml neomycin, for 16 hours at 30° C. Total DNA from these cultures was isolated (Holmes et al., *Anal. Biochem.* (1981) 114:193–197). The absence of plasmids in these cells was verified by DNA electrophoresis on agarose gels. Samples in which low molecular weight DNA was virtually absent, were rechecked for the presence of plasmid DNA by DNA transformation to *B. subtilis* 1-A40 (Spizizen et al., 1961). Samples lacking the ability to transform *B. subtilis* 1-A40 to neomycin resistance were considered plasmid minus.

To check whether integration of pElatB took place and how it took place, chromosomal DNA was isolated from the transformants (Saito-Minwa, *Biochem. Biophys. Acta* (1963) 72:619–632), digested with EcoRI, fractionated on 0.5% agarose gels, blotted onto nitro-cellulose filters (Southern, *J. Mol. Biol.* (1975) 98: 503–517) and hybridized with $^{32}$P-labeled nick-translated pGB33 (see EP-A-0134048). The results from this analysis are shown in FIG. 9A. The data show that illegitimate recombination of pElatB took place resulting in a strain containing a single amylase gene on a different locus of the genome as compared with the original *B. licheniformis* T5 amylase strain. The strain obtained containing pElatB was named TB13.

Example 11

Construction of Strain T13F Containing Two Amylase Genes Separated by Endogenous Chromosomal Sequences In order to develop a strain containing two amylase genes separated by endogenous chromosomal DNA sequences, a fusion experiment was performed between *B. licheniformis* strain T5 (the original amylase gene containing amylase strain, see EP-A-013048) and strain TB13 (the randomly integrated, amylase gene containing strain). *B. licheniformis* strain T5 was deposited as *B. licheniformis* T-5a at the Centraal Bureau voor Schimmelcultures, P.O. Box 273, 3740 AG BAARN, The Netherlands on Jun. 7, 1983 under Accession Number CBS 470.83 (LMD 83.16). Protoplast fusion was performed as described in EP-A-0134048, the disclosure of which is hereby incorporated by reference. Strain TB13 was killed with iodoacetamide prior to protoplast formation. Strain T5 (neomycin sensitive) was not killed. Selection for fusants took place on the regeneration plates containing 10 μg/ml neomycin.

To check and identify potential fusants, chromosomal DNA was isolated, digested with EcoRI, fractionated on 0.5% agarose gels, blotted to nitrocellulose filters (Southern, *J. Mol. Biol.* (1975) 98:503–517) and hybridized with $^{32}$P-labeled nick-translated pGB33 (see EP-A-0134048). The result of this analysis is shown in FIG. 9B. One of the obtained fusants, T13F, contained two amylase genes separated by endogenous chromosomal sequences.

Example 12

Stability of the Duplicated Amylase Genes in Strains T390 and T13F

The stability of-strain T13F, a strain containing two chromosomal amylase genes separated by essential chromosomal sequences, was compared with that of strain T390, a strain with two chromosomal amylase genes located in a tandem array. Preparation of strain T390 is disclosed in European application EP-A-0134048 (page 17, Table I), where it was referred to as B. licheniformis T5 (pGB33).

Strains T13F and T390 were tested under fermentation conditions, namely 0.2 ml of an overnight TSB culture (37° C.) was inoculated in 500 ml shake flasks containing 100 ml production medium (see Example 7; after sterilization the pH was adjusted to 6.9 with NaOH) without neomycin. After incubation for 6 days at 40° C. under constant aeration, the culture was tested for neomycin-resistant colonies and amylase activity. The results of the fermentation experiments are summarized in the following Table 2.

TABLE 2

| Strain | Relative Amylase Activity | Percent or Neomycin-Resistant Cells After Fermentation* |
|---|---|---|
| T5 | 100% | — |
| TB13 | 20% | 100% |
| T13F | 120% | 100% |
| T390 | 200% | 88% |

*More than a thousand colonies were tested per strain.

To exclude the possibility of excision of one amylase gene without concomitant loss of the neomycin gene in strain T13F, 20 colonies derived from the T13F fermentation were analyzed. Chromosomal DNA from 20 randomly chosen colonies was isolated and characterized by hybridization experiments as described above. The results of 9 of these analyses are shown in FIG. 10. All strains tested contained two amylase genes, as demonstrated by the presence of two α-amylase genes-containing EcoRI fragments in their chromosomal DNA.

In contrast to the genetic stability of strain T13F, strain T390 was found to be unstable upon fermentation resulting in 12% neomycin-sensitive colonies. One of these colonies was analyzed and found to contain only one α-amylase gene (FIG. 10, Lane 4). This shows that randomly integrated amylase genes are more stable than tandemly integrated genes, under fermentation conditions.

It is evident from the above results that a prokaryotic cell may be obtained in which stable gene amplification is achieved by selecting for transformed cells in which non-tandem integration of at least two copies of the structural gene to be amplified has occurred. Integration may occur by homologous recombination or illegitimate recombination.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A transformed prokaryotic host cell comprising at least two non-tandem copies of a DNA sequence encoding a polypeptide of interest, said cell being produced by a method comprising the steps of:

(1) combining a recipient prokaryotic host cell that can be transformed comprising at least one copy of said DNA sequence integrated into its chromosome with either
   (a) a DNA construct which provides for random, non-tandem integration into said host cell chromosome, comprising at least one copy of said DNA sequence and at least one selection means selected from the group consisting of a marker gene and a temperature-sensitive origin of replication, or
   (b) a donor host cell comprising said DNA construct, under transforming conditions to produce a transformed prokaryotic host cell;

(2) selecting for a plasmid-free transformed prokaryotic host cell comprising at least two non-tandem copies of said DNA sequence randomly integrated into its chromosome and separated by endogenous chromosomal DNA sequences in the genome of said host cell such that deletion of said endogenous chromosomal sequences as a result of recombination between said two copies of said DNA sequence is lethal to said host cell; and (3) isolating said plasmid-free transformed prokaryotic host cell, said prokaryotic host cell selected from the group consisting of *Escherichia coli,* Bacillus, Streptomyes, and Pseudomonas cells.

2. A transformed prokaryotic host cell according to claim 1, wherein said prokaryotic host cell is selected from the group consisting of *Escherichia coli* and Bacillus species.

3. A transformed prokaryotic host cell according to claim 1, wherein said polypeptide of interest is an enzyme.

4. A transformed prokaryotic host cell according to claim 1, wherein said DNA sequence is from the genome of a member of the same genus as said host cell.

5. A transformed prokaryotic host cell according to claim 1, wherein said DNA sequence is from the genome of *Bacillus licheniformis* T5 or Bacillus novo species PB92.

6. An isolated transformed prokaryotic host cell according to claim 1, wherein said random non-tandem integration is by illegitimate recombination.

7. An isolated transformed prokaryotic host cell according to claim 1, wherein said endogenous chromosomal DNA sequences are less than 10 kilobase pairs.

8. An isolated transformed prokaryotic host cell according to claim 1, wherein said DNA construct is linear.

9. A transformed prokaryotic host cell according to claim 3, wherein said enzyme is a proteolytic enzyme or an amylolytic enzyme.

10. A transformed prokaryotic host cell according to claim 9, wherein said proteolytic enzyme is a serine protease.

11. A transformed prokaryotic host cell according to claim 9, wherein said amylolytic enzyme is α-amylase.

12. A transformed prokaryotic host cell according to claim 8, wherein said serine protease comprises substantially the amino acid sequence corresponding to residues 1 to 269 of SEQ ID NO: 2:

H₂N–A–Q–S–V–P–W–G–I–S–R–V–Q–A–P–A–A–H–N–R–G–L–T–G–S–G–V–K–V–A–
V–L–D–T–G–I–S–T–H–P–D–L–N–I–R–G–G–A–S–F–V–P–G–E–P–S–T–Q–D–G–N–
G–H–G–T–H–V–A–G–T–I–A–A–L–N–N–S–I–G–V–L–G–V–A–P–N–A–E–L–Y–A–V–
K–V–L–G–A–S–G–S–G–S–V–S–S–I–A–Q–G–L–E–W–A–G–N–N–G–M–H–V–A–N–L–
S–L–G–S–P–S–P–S–A–T–L–E–Q–A–V–N–S–A–T–S–R–G–V–L–V–V–A–A–S–G–N–
S–G–A–G–S–I–S–Y–P–A–R–Y–A–N–A–M–A–V–G–A–T–D–G–N–N–N–R–A–S–F–S–
Q–Y–G–A–G–L–D–I–V–A–P–G–V–N–V–Q–S–T–Y–P–G–S–T–Y–A–S–L–N–G–T–S–
M–A–T–P–H–V–A–G–A–A–A–L–V–K–Q–K–N–P–S–W–S–N–V–Q–I–R–N–H–L–K–N–
T–A–T–S–L–G–S–T–N–L–Y–G–S–G–L–V–N–A–E–A–A–T–R–COOH.

13. A method for preparing a transformed prokaryotic host cell comprising at least two non-tandem copies of a DNA sequence encoding a polypeptide of interest, said method comprising the steps of:
 (1) combining a recipient prokaryotic host cell that can be transformed comprising at least one copy of said DNA sequence integrated into its chromosome with either
  (a) a DNA construct which provides for random, non-tandem integration into said host cell chromosome, comprising at least one copy of said DNA sequence and at least one selection means selected from the group consisting of a marker gene and a temperature-sensitive origin of replication, or
  (b) a donor cell comprising said DNA construct,
 under transforming conditions to produce a transformed prokaryotic host cell;
 (2) selecting for a plasmid-free transformed prokaryotic host cell comprising at least two non-tandem copies of said DNA sequence randomly integrated into its chromosome and separated by endogenous chromosomal DNA sequences in the genome of said host cell such that deletion of said endogenous chromosomal sequences as a result of recombination between said two copies of said DNA sequence is lethal to said host cell; and
 (3) isolating said plasmid-free transformed prokaryotic host cell, said prokaryotic host cell selected from the group consisting of *Escherichia coli*, Bacillus, Streptomyes, and Pseudomonas cells.

14. A method according to claim 13, wherein said selecting comprises:
 growing said transformant comprising a DNA construct comprising a marker gene in the presence of a biocide to which said marker gene provides resistance.

15. A method according to claim 13, wherein said selecting comprises:
 growing said transformant comprising a DNA construct comprising a marker gene and a temperature-sensitive origin of replication in the presence of a biocide at a non-permissive temperature.

16. A method according to claim 13, wherein said isolating comprises:
 isolating chromosomal DNA from said transformants; and
 hybridizing said chromosomal DNA with a labeled probe comprising said DNA construct whereby said transformed prokaryotic host cells are identified by detecting said label.

17. A method according to claim 13, wherein said donor cell is obtained by a method comprising:
 (1) combining a prokaryotic cell lacking a DNA sequence encoding said polypeptide of interest with said DNA construct under fusing conditions;
 (2) isolating transformed prokaryotic cells;
 (3) growing said transformed prokaryotic cells at a non-permissive temperature; and
 (4) identifying and isolating transformed prokaryotic cells wherein said DNA construct is integrated into a location on the chromosome of said donor cell different from the location of said DNA sequence in said recipient host cell.

18. A method according to claim 13, wherein said polypeptide of interest is an enzyme.

19. A method according to claim 13, wherein said DNA construct is pMAX-4 or pElatB.

20. A method according to claim 13, wherein said temperature sensitive origin of replication is obtained from plasmid pE194.

21. A method according to claim 18, wherein said enzyme is a serine protease or an amylase.

22. A method according to claim 21, wherein said serine protease has substantially the following amino acid sequence corresponding to residues 1 to 269 of SEQ ID NO: 2:

H₂N–A–Q–S–V–P–W–G–I–S–R–V–Q–A–P–A–A–H–N–R–G–L–T–G–S–G–V–K–V–A–
V–L–D–T–G–I–S–T–H–P–D–L–N–I–R–G–G–A–S–F–V–P–G–E–P–S–T–Q–D–G–N–
G–H–G–T–H–V–A–G–T–I–A–A–L–N–N–S–I–G–V–L–G–V–A–P–N–A–E–L–Y–A–V–
K–V–L–G–A–S–G–S–G–S–V–S–S–I–A–Q–G–L–E–W–A–G–N–N–G–M–H–V–A–N–L–
S–L–G–S–P–S–P–S–A–T–L–E–Q–A–V–N–S–A–T–S–R–G–V–L–V–V–A–A–S–G–N–
S–G–A–G–S–I–S–Y–P–A–R–Y–A–N–A–M–A–V–G–A–T–D–G–N–N–N–R–A–S–F–S–
Q–Y–G–A–G–L–D–I–V–A–P–G–V–N–V–Q–S–T–Y–P–G–S–T–Y–A–S–L–N–G–T–S–
M–A–T–P–H–V–A–G–A–A–A–L–V–K–Q–K–N–P–S–W–S–N–V–Q–I–R–N–H–L–K–N–
T–A–T–S–L–G–S–T–N–L–Y–G–S–G–L–V–N–A–E–A–A–T–R–COOH.

23. A method according to claim 21, wherein said polypeptide of interest is a serine protease whose coding sequence has at least 70% homology with the nucleic acid that encoded the following amino acid sequence corresponding to residues 1 to 269 of SEQ ID NO: 2:

H₂N—A—Q—S—V—P—W—G—I—S—R—V—Q—A—P—A—A—H—N—R—G—L—T—G—S—G—V—K—V—A—
V—L—D—T—G—I—S—T—H—P—D—L—N—I—R—G—G—A—S—F—V—P—G—E—P—S—T—Q—D—G—N—
G—H—G—T—H—V—A—G—T—I—A—A—L—N—N—S—I—G—V—L—G—V—A—P—N—A—E—L—Y—A—V—
K—V—L—G—A—S—G—S—G—S—V—S—S—I—A—Q—G—L—E—W—A—G—N—N—G—M—H—V—A—N—L—
S—L—G—S—P—S—P—S—A—T—L—E—Q—A—V—N—S—A—T—S—R—G—V—L—V—V—A—A—S—G—N—
S—G—A—G—S—I—S—Y—P—A—R—Y—A—N—A—M—A—V—G—A—T—D—G—N—N—N—R—A—S—F—S—
Q—Y—G—A—G—L—D—I—V—A—P—G—V—N—V—Q—S—T—Y—P—G—S—T—Y—A—S—L—N—G—T—S—
M—A—T—P—H—V—A—G—A—A—A—L—V—K—Q—K—N—P—S—W—S—N—V—Q—I—R—N—H—L—K—N—
T—A—T—S—L—G—S—T—N—L—Y—G—S—G—L—V—N—A—E—A—A—T—R—COOH.

24. An isolated transformed prokaryotic host cell comprising at least two non-tandem copies of a DNA sequence encoding a polypeptide of interest randomly integrated into the chromosome and separated by endogenous chromosomal sequences in the genome of said host cell, whereby the at least two non-tandem copies of a DNA sequence encoding a polypeptide of interest are stably present in the genome, and wherein said non-tandem copies of said DNA sequence and said endogenous chromosomal sequences permit selection for said transformed prokaryotic host cell and deletion of said endogenous chromosomal sequences in the genome of said host cell as a result of recombination between the two copies of said DNA sequence is lethal to said host cell, said prokaryotic host cell selected from the group consisting of *Escherichia coli,* Bacillus, Streptomyces and Pseudomonas cells.

* * * * *

SEQUENCE LISTING

```
(1) GENERAL INFORMATION:

(iii) NUMBER OF SEQUENCES: 2

(2) INFORMATION FOR SEQ ID NO: 1:

(i) SEQUENCE CHARACTERISTICS:
        (A) LENGTH: 1350 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iii) ANTI-SENSE: NO (vi) ORIGINAL SOURCE:
        (A) ORGANISM: Bacillus sp.
        (B) STRAIN: PB92

(ix) FEATURE:
        (A) NAME/KEY: CDS
        (B) LOCATION: 115..1257

(ix) FEATURE:
        (A) NAME/KEY: sig_peptide
        (B) LOCATION: 115..195

(ix) FEATURE:
        (A) NAME/KEY: misc_RNA
        (B) LOCATION: 196..447
        (D) OTHER INFORMATION: /function= "propeptide"
```

-continued (ix) FEATURE:
    (A) NAME/KEY: mat_peptide
    (B) LOCATION: 448..1257
    (D) OTHER INFORMATION: /product= "alkaline protease"

(xi) SEQUENCE DESCRIPTION: SEQ ID NO: 1:

```
GATTCTGTTA ACTTAACGTT AATATTTGTT TCCCAATAGG CAAATCTTTC TAACTTTGAT      60

ACGGTTTAAA CTACCAGCTT GGACAAGTTG GGATAAAAAT GAGGAGGGAA CCGA ATG       117
                                                            Met
                                                            -111

AAG AAA CCG TTG GGG AAA ATT GTC GCA AGC ACC GCA CTA CTC ATT TCT       165
Lys Lys Pro Leu Gly Lys Ile Val Ala Ser Thr Ala Leu Leu Ile Ser
-110            -105                -100                -95

GTT GCT TTT AGT TCA TCG ATC GCA TCG GCT GCT GAA GAA GCA AAA GAA       213
Val Ala Phe Ser Ser Ser Ile Ala Ser Ala Ala Glu Glu Ala Lys Glu
                -90                 -85                 -80

AAA TAT TTA ATT GGC TTT AAT GAG CAG GAA GCT GTC AGT GAG TTT GTA       261
Lys Tyr Leu Ile Gly Phe Asn Glu Gln Glu Ala Val Ser Glu Phe Val
            -75                 -70                 -65

GAA CAA GTA GAG GCA AAT GAC GAG GTC GCC ATT CTC TCT GAG GAA GAG       309
Glu Gln Val Glu Ala Asn Asp Glu Val Ala Ile Leu Ser Glu Glu Glu
        -60                 -55                 -50

GAA GTC GAA ATT GAA TTG CTT CAT GAA TTT GAA ACG ATT CCT GTT TTA       357
Glu Val Glu Ile Glu Leu Leu His Glu Phe Glu Thr Ile Pro Val Leu
-45                 -40                 -35

TCC GTT GAG TTA AGC CCA GAA GAT GTG GAC GCG CTT GAA CTC GAT CCA       405
Ser Val Glu Leu Ser Pro Glu Asp Val Asp Ala Leu Glu Leu Asp Pro
-30                 -25                 -20                 -15

GCG ATT TCT TAT ATT GAA GAG GAT GCA GAA GTA ACG ACA ATG GCG CAA       453
Ala Ile Ser Tyr Ile Glu Glu Asp Ala Glu Val Thr Thr Met Ala Gln
            -10                 -5                   1

TCA GTG CCA TGG GGA ATT AGC CGT GTG CAA GCC CCA GCT GCC CAT AAC       501
Ser Val Pro Trp Gly Ile Ser Arg Val Gln Ala Pro Ala Ala His Asn
        5                   10                  15

CGT GGA TTG ACA GGT TCT GGT GTA AAA GTT GCT GTC CTC GAT ACA GGT       549
Arg Gly Leu Thr Gly Ser Gly Val Lys Val Ala Val Leu Asp Thr Gly
    20                  25                  30

ATT TCC ACT CAT CCA GAC TTA AAT ATT CGT GGT GGC GCT AGC TTT GTA       597
Ile Ser Thr His Pro Asp Leu Asn Ile Arg Gly Gly Ala Ser Phe Val
35                  40                  45                  50

CCA GGG GAA CCA TCC ACT CAA GAT GGG AAT GGG CAT GGC ACG CAT GTG       645
Pro Gly Glu Pro Ser Thr Gln Asp Gly Asn Gly His Gly Thr His Val
                55                  60                  65

GCT GGG ACG ATT GCT GCT TTA AAC AAT TCG ATT GGC GTT CTT GGC GTA       693
Ala Gly Thr Ile Ala Ala Leu Asn Asn Ser Ile Gly Val Leu Gly Val
            70                  75                  80

GCA CCG AAC GCG GAA CTA TAC GCT GTT AAA GTA TTA GGG GCG AGC GGT       741
Ala Pro Asn Ala Glu Leu Tyr Ala Val Lys Val Leu Gly Ala Ser Gly
        85                  90                  95

TCA GGT TCG GTC AGC TCG ATT GCC CAA GGA TTG GAA TGG GCA GGG AAC       789
Ser Gly Ser Val Ser Ser Ile Ala Gln Gly Leu Glu Trp Ala Gly Asn
100                 105                 110

AAT GGC ATG CAC GTT GCT AAT TTG AGT TTA GGA AGC CCT TCG CCA AGT       837
Asn Gly Met His Val Ala Asn Leu Ser Leu Gly Ser Pro Ser Pro Ser
115                 120                 125                 130

GCC ACA CTT GAG CAA GCT GTT AAT AGC GCG ACT TCT AGA GGC GTT CTT       885
Ala Thr Leu Glu Gln Ala Val Asn Ser Ala Thr Ser Arg Gly Val Leu
                135                 140                 145

GTT GTA GCG GCA TCT GGG AAT TCA GGT GCA GGC TCA ATC AGC TAT CCG       933
Val Val Ala Ala Ser Gly Asn Ser Gly Ala Gly Ser Ile Ser Tyr Pro
```

```
            150                 155                 160
GCC CGT TAT GCG AAC GCA ATG GCA GTC GGA GCT ACT GAC CAA AAC AAC          981
Ala Arg Tyr Ala Asn Ala Met Ala Val Gly Ala Thr Asp Gln Asn Asn
        165                 170                 175

AAC CGC GCC AGC TTT TCA CAG TAT GGC GCA GGG CTT GAC ATT GTC GCA         1029
Asn Arg Ala Ser Phe Ser Gln Tyr Gly Ala Gly Leu Asp Ile Val Ala
        180                 185                 190

CCA GGT GTA AAC GTG CAG AGC ACA TAC CCA GGT TCA ACG TAT GCC AGC         1077
Pro Gly Val Asn Val Gln Ser Thr Tyr Pro Gly Ser Thr Tyr Ala Ser
195                 200                 205                 210

TTA AAC GGT ACA TCG ATG GCT ACT CCT CAT GTT GCA GGT GCA GCA GCC         1125
Leu Asn Gly Thr Ser Met Ala Thr Pro His Val Ala Gly Ala Ala Ala
            215                 220                 225

CTT GTT AAA CAA AAG AAC CCA TCT TGG TCC AAT GTA CAA ATC CGC AAT         1173
Leu Val Lys Gln Lys Asn Pro Ser Trp Ser Asn Val Gln Ile Arg Asn
            230                 235                 240

CAT CTA AAG AAT ACG GCA ACG AGC TTA GGA AGC ACG AAC TTG TAT GGA         1221
His Leu Lys Asn Thr Ala Thr Ser Leu Gly Ser Thr Asn Leu Tyr Gly
            245                 250                 255

AGC GGA CTT GTC AAT GCA GAA GCG GCA ACA CGC TAATCAATAA AAAAACGCTG      1274
Ser Gly Leu Val Asn Ala Glu Ala Ala Thr Arg
        260                 265

TGCTTAAAGG GCACAGCGTT TTTTTGTGTA TGAATCGAAA AAGAGAACAG ATCGCAGGTC      1334

TTATCGCTAT ACAATG                                                      1350

(2) INFORMATION FOR SEQ ID NO: 2:

(i) SEQUENCE CHARACTERISTICS:
        (A) LENGTH: 380 amino acids
        (B) TYPE: amino acid
        (D) TOPOLOGY: linear (ii) MOLECULE TYPE: protein (xi) SEQUENCE DESCRIPTION: SEQ ID NO: 2:

Met Lys Lys Pro Leu Gly Lys Ile Val Ala Ser Thr Ala Leu Leu Ile
-111-110            -105                -100

Ser Val Ala Phe Ser Ser Ile Ala Ser Ala Ala Glu Glu Ala Lys
-95                 -90                 -85                 -80

Glu Lys Tyr Leu Ile Gly Phe Asn Glu Gln Glu Ala Val Ser Glu Phe
                -75                 -70                 -65

Val Glu Gln Val Glu Ala Asn Asp Glu Val Ala Ile Leu Ser Glu Glu
            -60                 -55                 -50

Glu Glu Val Glu Ile Glu Leu Leu His Glu Phe Glu Thr Ile Pro Val
        -45                 -40                 -35

Leu Ser Val Glu Leu Ser Pro Glu Asp Val Asp Ala Leu Glu Leu Asp
    -30                 -25                 -20

Pro Ala Ile Ser Tyr Ile Glu Glu Asp Ala Glu Val Thr Thr Met Ala
-15                 -10                 -5                  1

Gln Ser Val Pro Trp Gly Ile Ser Arg Val Gln Ala Pro Ala Ala His
            5                   10                  15

Asn Arg Gly Leu Thr Gly Ser Gly Val Lys Val Ala Val Leu Asp Thr
        20                  25                  30

Gly Ile Ser Thr His Pro Asp Leu Asn Ile Arg Gly Gly Ala Ser Phe
        35                  40                  45

Val Pro Gly Glu Pro Ser Thr Gln Asp Gly Asn Gly His Gly Thr His
50                  55                  60                  65
```

-continued

```
Val Ala Gly Thr Ile Ala Ala Leu Asn Asn Ser Ile Gly Val Leu Gly
            70                  75                  80

Val Ala Pro Asn Ala Glu Leu Tyr Ala Val Lys Val Leu Gly Ala Ser
            85                  90                  95

Gly Ser Gly Ser Val Ser Ser Ile Ala Gln Gly Leu Glu Trp Ala Gly
        100                 105                 110

Asn Asn Gly Met His Val Ala Asn Leu Ser Leu Gly Ser Pro Ser Pro
        115                 120                 125

Ser Ala Thr Leu Glu Gln Ala Val Asn Ser Ala Thr Ser Arg Gly Val
130                 135                 140                 145

Leu Val Val Ala Ala Ser Gly Asn Ser Gly Ala Gly Ser Ile Ser Tyr
            150                 155                 160

Pro Ala Arg Tyr Ala Asn Ala Met Ala Val Gly Ala Thr Asp Gln Asn
            165                 170                 175

Asn Asn Arg Ala Ser Phe Ser Gln Tyr Gly Ala Gly Leu Asp Ile Val
            180                 185                 190

Ala Pro Gly Val Asn Val Gln Ser Thr Tyr Pro Gly Ser Thr Tyr Ala
        195                 200                 205

Ser Leu Asn Gly Thr Ser Met Ala Thr Pro His Val Ala Gly Ala Ala
210                 215                 220                 225

Ala Leu Val Lys Gln Lys Asn Pro Ser Trp Ser Asn Val Gln Ile Arg
            230                 235                 240

Asn His Leu Lys Asn Thr Ala Thr Ser Leu Gly Ser Thr Asn Leu Tyr
            245                 250                 255

Gly Ser Gly Leu Val Asn Ala Glu Ala Ala Thr Arg
        260                 265
```